United States Patent
Ochiai et al.

(10) Patent No.: US 7,192,608 B2
(45) Date of Patent: Mar. 20, 2007

(54) METHOD OF MANUFACTURING DRUG GRANULES, THE DRUG GRANULES AND PHARMACEUTICAL PREPARATION CONTAINING THE DRUG GRANULES

(75) Inventors: Yasushi Ochiai, Suita (JP); Kouji Wakisaka, Takatsuki (JP)

(73) Assignee: Sumitomo Pharmaceuticals Company Limited, Osaka (JP)

( * ) Notice: Subject to any disclaimer, the term of this patent is extended or adjusted under 35 U.S.C. 154(b) by 0 days.

(21) Appl. No.: 10/091,559

(22) Filed: Mar. 7, 2002

(65) Prior Publication Data

US 2003/0039699 A1    Feb. 27, 2003

(30) Foreign Application Priority Data

Mar. 7, 2001    (JP)    ............... 2001-064056

(51) Int. Cl.
- *A61K 9/16* (2006.01)
- *A61K 9/14* (2006.01)
- *A61K 9/20* (2006.01)
- *A61K 9/22* (2006.01)
- *A61K 9/26* (2006.01)

(52) U.S. Cl. ............... 424/490; 424/489; 424/497; 424/464; 424/468; 424/469; 424/470

(58) Field of Classification Search ............... 424/490, 424/489, 497, 464, 468, 469, 470
See application file for complete search history.

(56) References Cited

U.S. PATENT DOCUMENTS 5,300,318 A * 4/1994 Pierre et al. ............... 427/212
5,855,914 A * 1/1999 Koyama et al.

FOREIGN PATENT DOCUMENTS

| EP | 0380219 A2 | 8/1990 |
|---|---|---|
| EP | 0465337 A1 | 1/1992 |
| EP | 0786526 A2 | 7/1997 |
| GB | 1109425 A | 4/1968 |
| GB | 1109425 A * | 4/1968 |
| JP | 5-229961 | 9/1993 |
| JP | 9-175999 | 7/1997 |
| JP | 9-263589 | 10/1997 |
| JP | 9-295947 | 11/1997 |
| JP | 10-139659 | 5/1998 |
| JP | 11-92403 | 4/1999 |
| WO | WO99/04760 | 2/1999 |

* cited by examiner

*Primary Examiner*—Humera N. Sheikh
(74) *Attorney, Agent, or Firm*—Birch, Stewart, Kolasch & Birch, LLP

(57) ABSTRACT

The present invention provides coated granules using drug granules containing a water soluble drug as an active ingredient at a high density, which is superior in uniform content and stability, and which is capable of providing a pharmaceutical preparation superior in drug release control and having a smaller size than conventional preparations, and a production method of the granules, and further, a pharmaceutical preparation using the drug granules.

2 Claims, 19 Drawing Sheets

METHOD OF MANUFACTURING DRUG GRANULES, THE DRUG GRANULES AND PHARMACEUTICAL PREPARATION CONTAINING THE DRUG GRANULES

TECHNICAL FIELD OF THE INVENTION

The present invention relates to a method of manufacturing drug granules, which comprises granulating crystals of a water soluble drug by spraying a solution of said water soluble drug, a method of manufacturing drug granules having a granular strength of 650–2500 gf/mm$^2$, which comprises a granulation step of spraying only a solution of a water soluble drug on crystals of said water soluble drug, substantially without using a binder or in the absence of a binder, and the drug granules obtained thereby. The present invention also relates to a pharmaceutical preparation containing drug granules obtained or obtainable by granulating crystals of a water soluble drug by spraying a solution of the water soluble drug, and a pharmaceutical preparation containing a drug granule having a granular strength of 650–2500 gf/mm$^2$, which is obtained or obtainable by a method comprising a granulation step of spraying only a solution of a water soluble drug on a crystal of the water soluble drug, substantially without using a binder or in the absence of a binder. Furthermore, the present invention also relates to a coated granule obtained or obtainable by coating, with a release control film coating agent, a drug granule obtained or obtainable by a method comprising a granulation step of spraying a solution of a water soluble drug on a crystal of the water soluble drug and a method of manufacture thereof, as well as a coated granule obtained or obtainable by coating, with a release control film coating agent, a drug granule having a granular strength of 650–2500 gf/mm$^2$, which is obtained or obtainable by a method comprising a granulation step of spraying only a solution of a water soluble drug on a crystal of the water soluble drug, substantially without using a binder or in the absence of a binder, and a production method thereof.

BACKGROUND OF THE INVENTION

In general terms, conventional oral preparations having high drug dose are hard to administer, because they tend to be bulky. A drug of low aqueous solubility has a difficulty in minimizing its size because certain design for the preparation is necessary for improving dissolution rate and the like to ensure sufficient efficacy. A drug having high water solubility is formed into tablets along with a small amount of excipients and the like, or the single crystal thereof is filled in a capsule to form a capsule preparation or in a dispense package to give a granule preparation. For production of tablets, some additives are necessary, but certain drugs do not permit addition of other substances in view of the stability. In this event, single crystal of the drug is directly filled in a capsule to form a capsule preparation or directly formed into granule preparation or powder preparation. The use of a drug in the form of single crystal leads to low flowability, which in turn produces variation in the amount to be contained in a capsule preparation or a folded piece preparation, thereby failing to ensure uniform content, or sometimes even filling itself. When packaged in a bottle and the like, an easy measure using a measure spoon and the like may become unattainable.

Generally, when a tablet preparation or capsule preparation containing a water soluble drug is orally administered; the blood concentration of the drug tends to increase in an initial stage and drastically falls thereafter. Such dissolution pattern of a drug does not maintain a desired blood concentration or efficacy of the drug. Thus, tablet preparation and capsule preparation of such water soluble drugs mostly fail to show sufficient potential of a water soluble drug, thereby limiting its clinical usefulness.

Starting from the 1970s, many attempts to improve drug release have been made by introducing various drug delivery systems. For example, it is now possible to prevent drastic increase in blood concentration and improve insufficient retention in the concentration range necessary for treatment, by controlling release of a drug from a preparation to a constant level. There are some preparations that have enabled a single administration per day of a drug having a short half-life time in the body, by controlling migration in the gastrointestinal tract. In addition, targeting of absorption site in the gastrointestinal tract and lesion has become available by a drug release at a desired time after intake and control of a drug release at a desired site in the digestive tract, thereby enabling administration in advance of a drug, avoiding the time period when drug intake is difficult. This in turn has afforded effective drug treatment while reducing side effects, improvement of QOL (Quality of Life) of patients as a result of reduced frequency of administration, and ensured drug treatment based on improved compliance.

On the contrary, the aforementioned techniques relating to preparations for oral administration defy easy application to water soluble drugs. In most cases, drug release of such drugs is controlled by the use of polymer matrix comprising a combination of various polymers and the like and film coating of various polymers and the like. In the case of the above-mentioned polymer matrix, however, the amount of a release control ingredient generally used has been insufficient to achieve suitable control of a drug release rate using a drug having extremely high aqueous solubility. To compensate this, the amount of a release control ingredient is increased, which problematically makes preparations bulky or large in size. In the case of the above-mentioned film coating, burst after administration has a risk of causing serious side effects because it is a single-unit type preparation.

Therefore, a multiple-unit type drug release control by coating various polymers and the like is considered to be more superior. However, the multiple-unit type release control requires increased amount of release control film coating agents to obtain a desired dissolution pattern of a water soluble drug. An attempt has been made to decrease the size of preparation by reducing the amount of additives other than the release control film coating agent. For example, direct coating of a single crystal of a water soluble drug has been reported. However, the use of a single crystal as it is is associated with difficulty in desirably controlling the release, because a single crystal of a water soluble drug has a large surface area due to its shape. To achieve the desired release control, the amount of a release control film coating agent needs to be increased, which prevents minimizing the size of preparations. In particular, the size of preparation and the like may pose a problem in the case of oral administration to elderly people. Thus, an oral pharmaceutical preparation free of such problems has been desired in clinical situations.

SUMMARY OF THE INVENTION

It is therefore an object of the present invention to provide a pharmaceutical preparation containing a water soluble drug as an active ingredient at a high density, which shows superior stability and a uniform content. Another object of the present invention is to provide a drug granule capable of minimizing the size of a pharmaceutical preparation superior to conventional ones in drug release control, and a manufacturing method thereof. Another object of the present invention is to provide a coated granule containing high dose of a water soluble drug as an active ingredient, which show a uniform content and superior stability, and a production method thereof.

A further object of the present invention is to provide a pharmaceutical preparation containing high dose of a water soluble drug as an active ingredient, which is substantially free of a binder, and which show a uniform content and superior stability. Another object of the present invention is to provide a granule of a water soluble drug substantially free of a binder, and a manufacturing method thereof. A further object of the present invention is to provide a coated granule substantially free of a binder, which comprises a drug granule containing high dose of a water soluble drug as an active ingredient and which shows superior stability and a uniform content, and a production method thereof.

As a result of intensive studies by the present inventors, it has been found that a drug granule, for a pharmaceutical preparation containing high dose of a water soluble drug and having desired drug release ability, can be obtained or obtainable by a method comprising a granulation step of spraying a solution of a water soluble drug on a crystal of the water soluble drug without using a core, which is a physiologically inactive substance, or a binding substance, and that drug granule having a granular strength of 650–2500 gf/mm$^2$, which afford a pharmaceutical preparation containing a high dose of the drug and having desired drug releaseability can be obtained or obtainable by a method comprising a granulation step of spraying a solution of a water soluble drug on a crystal of the water soluble drug, without using a core, which is a physiologically inactive substance, and substantially without a binder or in the absence of a binder.

Accordingly, the present invention relates to:

(1) a drug granule obtained or obtainable by a method comprising a granulation step of spraying a solution of a water soluble drug on a crystal of said water soluble drug;

(1') the drug granule of the above-mentioned (1) having a granular strength of 650–2500 gf/mm$^2$, which is obtained or obtainable by a method comprising a granulation step of spraying only a solution of a water soluble drug on a crystal of said water soluble drug, substantially without using a binder or in the absence of a binder;

(2) the drug granule of the above-mentioned (1), wherein the water soluble drug has an aqueous solubility of not less than 5% (W/W);

(3) the drug granule of the above-mentioned (1), wherein the water soluble drug has an aqueous solubility of not less than 10% (W/W);

(4) the drug granule of the above-mentioned (1), wherein the water soluble drug has an aqueous solubility of not less than 20% (W/W);

(5) the drug granule of any of the above-mentioned (1) to (4), wherein the granule has a particle size of 0.05 mm–1.5 mm;

(6) the drug granule of any of the above-mentioned (1) to (4), wherein the granule has a particle size of 0.1 mm–1 mm;

(7) the drug granule of any of the above-mentioned (1) to (4), wherein the granule has a particle size of 0.3 mm–1 mm;

(8) the drug granule of any of the above-mentioned (1) to (4), wherein the granule has a particle size of 0.5 mm–0.9 mm;

(9) the drug granule of any of the above-mentioned (1) to (4), wherein the granule has a particle size of 0.1 mm–0.5 mm;

(10) the drug granule of any of the above-mentioned (1) to (4), wherein the granule has a particle size of 0.2 mm–0.4 mm;

(11) the drug granule of the above-mentioned (1), wherein the water soluble drug is N,N-dimethylimidodicarbonimidicdiamide, N-butylimidodicarbonimidicdiamide, N-(2-phenylethyl) imidodicarbonimidicdiamide, (1-hydroxyethylidene) bis-phosphonate, (4-amino-1-hydroxybutylidene) bis-phosphonate, (dichloromethylene) bis-phosphonate, ascorbic acid, sodium ascorbate, ethosuximide, sodium valproate, phenytoin sodium, amitriptyline hydrochloride, imipramine hydrochloride, lithium citrate, caffeine citrate, amantadine hydrochloride, chlorpromazine hydrochloride, thioridazine hydrochloride, meclofenoxate hydrochloride, oxytetracycline hydrochloride, talampicillin hydrochloride, tetracycline hydrochloride, pivmecillinum hydrochloride, vancomycin hydrochloride, lincomycin hydrochloride, potassium clavulanate, cephradine, kanamycin sulfate, fradiomycin sulfate, cloxacillin sodium, dicloxacillin sodium, tolperisone hydrochloride, chloral hydrate, acebutolol hydrochloride, procainamide hydrochloride, mexiletine hydrochloride, trapidil, diethyl carbamazine citrate, potassium bromide, sodium bromide, tranexamic acid, sodium cromoglicate, antipyrine, sodium salicylate, tiaramide hydrochloride, sulpyrine, naproxen sodium, migrenin, isoniazid, potassium iodide, potassium chloride, calcium chloride, sodium chloride, ethylcysteine hydrochloride, procarbazine hydrochloride, ranitidine hydrochloride, penicillamine, penicillamine hydrochloride, flavoxate hydrochloride, hexamine mandelate, alprenolol hydrochloride, indenolol hydrochloride, oxprenolol hydrochloride, verapamil hydrochloride, flecainide acetate, metoprolol tartarate, diltiazem hydrochloride, propranolol hydrochloride, captopril, papaverine hydrochloride, phenobarbital sodium, clomipramine hydrochloride, diphenhydramine hydrochloride, hydroxyzine hydrochloride, promethazine hydrochloride, doxycycline hydrochloride, noscapine hydrochloride, hydrocotarnine hydrochloride, dl-methylephedrine hydrochloride, pentoxyverine citrate, orciprenaline sulfate, phenylpropanolamine hydrochloride, potassium guaiacolsulfonate, pyridoxine hydrochloride, fursultiamine hydrochloride, niacinamide, calcium pantothenate, pethidine hydrochloride, loxoprofen sodium, cyanamide, pyridostigmine bromide, iron II sulfide, or a pharmaceutically acceptable salt thereof;

(11') the drug granule of the above-mentioned (1), wherein the water soluble drug is N,N-dimethylimidodicarbonimidicdiamide, N-butylimidodicarbonimidicdiamide, N-(2-phenylethyl) imidodicarbonimidicdiamide, (1-hydroxyethylidene) bis-phosphonate, (4-amino-1-hydroxybutylidene) bis-phosphonate, (dichloromethylene) bis-phosphonate, ascorbic acid, sodium ascorbate, gabapentin, ethosuximide, sodium valproate, phenytoin sodium, amitriptyline hydrochloride, imipramine hydrochloride, lithium citrate, caffeine citrate, amantadine hydrochloride, chlorpromazine hydrochloride, thioridazine hydrochloride, meclofenoxate hydrochloride, oxytetracycline hydrochloride, talampicillin hydrochloride, tetracycline hydrochloride, pivmecillinum hydrochloride, vancomycin hydrochloride, lincomycin hydrochloride, potassium clavulanate, cephradine, kanamycin sulfate, fradiomycin sulfate, cloxacillin sodium, dicloxacillin sodium, ciprofloxacin hydrochloride, amoxicillin, tolperisone hydrochloride, chloral hydrate, acebutolol hydrochloride, procainamide hydrochloride, mexiletine hydrochloride, trapidil, diethyl carbamazine citrate, potassium bromide, sodium bromide, tranexamic acid, sodium cromoglicate, antipyrine, sodium salicylate, tiaramide hydrochloride, sulpyrine, naproxen sodium, migrenin, isoniazid, potassium iodide, potassium chloride, calcium chloride, sodium chloride, ethylcysteine hydrochloride, procarbazine hydrochloride, cimetidine, ranitidine hydrochloride, penicillamine, penicillamine hydrochloride, flavoxate hydrochloride, hexamine mandelate, alprenolol hydrochloride, indenolol hydrochloride, oxprenolol hydrochloride, verapamil hydrochloride, flecainide acetate, metoprolol tartarate, diltiazem hydrochloride, propranolol hydrochloride, captopril, papaverine hydrochloride, phenobarbital sodium, clomipramine hydrochloride, diphenhydramine hydrochloride, hydroxyzine hydrochloride, promethazine hydrochloride, doxycycline hydrochloride, noscapine hydrochloride, hydrocotarnine hydrochloride, dl-methylephedrine hydrochloride, pentoxyverine citrate, orciprenaline sulfate, phenylpropanolamine hydrochloride, carbocisteine, potassium guaiacolsulfonate, pyridoxine hydrochloride, fursultiamine hydrochloride, niacinamide, calcium pantothenate, pethidine hydrochloride, loxoprofen sodium, cyanamide, pyridostigmine bromide, iron II sulfide, or a pharmaceutically acceptable salt thereof;

(12) the drug granule of the above-mentioned (1), wherein the water soluble drug is N,N-dimethylimidodicarbonimidicdiamide, N-butylimidodicarbonimidicdiamide, N-(2-phenylethyl) imidodicarbonimidicdiamide, (1-hydroxyethylidene) bis-phosphonate, (4-amino-1-hydroxybutylidene) bis-phosphonate, (dichloromethylene) bis-phosphonate, ascorbic acid, sodium ascorbate, ethosuximide, sodium valproate, phenytoin sodium, amitriptyline hydrochloride, imipramine hydrochloride, lithium citrate, caffeine citrate, amantadine hydrochloride, chlorpromazine hydrochloride, thioridazine hydrochloride, meclofenoxate hydrochloride, oxytetracycline hydrochloride, talampicillin hydrochloride, tetracycline hydrochloride, pivmecillinum hydrochloride, vancomycin hydrochloride, lincomycin hydrochloride, potassium clavulanate, cephradine, kanamycin sulfate, fradiomycin sulfate, cloxacillin sodium, dicloxacillin sodium, tolperisone hydrochloride, chloral hydrate, acebutolol hydrochloride, procainamide hydrochloride, mexiletine hydrochloride, trapidil, diethyl carbamazine citrate, potassium bromide, sodium bromide, tranexamic acid, sodium cromoglicate, antipyrine, sodium salicylate, tiaramide hydrochloride, sulpyrine, naproxen sodium, migrenin, isoniazid, potassium iodide, potassium chloride, calcium chloride, sodium chloride, ethylcysteine hydrochloride, procarbazine hydrochloride, ranitidine hydrochloride, penicillamine, penicillamine hydrochloride, flavoxate hydrochloride, hexamine mandelate, or a pharmaceutically acceptable salt thereof;

(12') the drug granule of the above-mentioned (1), wherein the water soluble drug is N,N-dimethylimidodicarbonimidicdiamide, N-butylimidodicarbonimidicdiamide, N-(2-phenylethyl) imidodicarbonimidicdiamide, (1-hydroxyethylidene) bis-phosphonate, (4-amino-1-hydroxybutylidene) bis-phosphonate, (dichloromethylene) bis-phosphonate, ascorbic acid, sodium ascorbate, gabapentin, ethosuximide, sodium valproate, phenytoin sodium, amitriptyline hydrochloride, imipramine hydrochloride, lithium citrate, caffeine citrate, amantadine hydrochloride, chlorpromazine hydrochloride, thioridazine hydrochloride, meclofenoxate hydrochloride, oxytetracycline hydrochloride, talampicillin hydrochloride, tetracycline hydrochloride, pivmecillinum hydrochloride, vancomycin hydrochloride, lincomycin hydrochloride, potassium clavulanate, cephradine, kanamycin sulfate, fradiomycin sulfate, cloxacillin sodium, dicloxacillin sodium, ciprofloxacin hydrochloride, amoxicillin, tolperisone hydrochloride, chloral hydrate, acebutolol hydrochloride, procainamide hydrochloride, mexiletine hydrochloride, trapidil, diethyl carbamazine citrate, potassium bromide, sodium bromide, tranexamic acid, sodium cromoglicate, antipyrine, sodium salicylate, tiaramide hydrochloride, sulpyrine, naproxen sodium, migrenin, isoniazid, potassium iodide, potassium chloride, calcium chloride, sodium chloride, ethylcysteine hydrochloride, procarbazine hydrochloride, cimetidine, ranitidine hydrochloride, penicillamine, penicillamine hydrochloride, flavoxate hydrochloride, hexamine mandelate, carbocisteine, or a pharmaceutically acceptable salt thereof;

(13) the drug granule of the above-mentioned (1), wherein the water soluble drug is N,N-dimethylimidodicarbonimidicdiamide, N-butylimidodicarbonimidicdiamide, or a pharmaceutically acceptable salt thereof;

(13') the drug granule of the above-mentioned (1), wherein the water soluble drug is N,N-dimethylimidodicarbonimidicdiamide, N-butylimidodicarbonimidicdiamide, N-(2-phenylethyl) imidodicarbonimidicdiamide, (1-hydroxyethylidene) bis-phosphonate, (4-amino-1-hydroxybutylidene) bis-phosphonate, (dichloromethylene) bis-phosphonate, gabapentin, ciprofloxacin hydrochloride, sodium valproate, potassium clavulanate, amoxicillin, mexiletine hydrochloride, tranexamic acid, carbocisteine, loxoprofen sodium, ranitidine hydrochloride or a pharmaceutically acceptable salt thereof;

(14) a coated granule obtained or obtainable by a method comprising a step of coating, with a sustained release film coating agent, a drug granule obtained or obtainable by a method comprising a granulation step of spraying a solution of a water soluble drug on a crystal of said water soluble drug;

(14') the coated granule of the above-mentioned (14), wherein the drug granule is obtained or obtainable by a method comprising a granulation step of spraying only a solution of a water soluble drug on a crystal of said water soluble drug, substantially without using a binder or in the absence of a binder, and wherein the drug granule has a granular strength of 650–2500 gf/mm$^2$;

(15) the coated granule of the above-mentioned (14), wherein the water soluble drug has an aqueous solubility of not less than 5% (W/W);

(16) the coated granule of the above-mentioned (14), wherein the water soluble drug has an aqueous solubility of not less than 10% (W/W);

(17) the coated granule of the above-mentioned (14), wherein the water soluble drug has an aqueous solubility of not less than 20% (W/W);

(18) the coated granule of any of the above-mentioned (14) to (17), wherein the drug granule has a particle size of 0.05 mm–1.5 mm;

(19) the coated granule of any of the above-mentioned (14) to (17), wherein the drug granule has a particle size of 0.1 mm–1 mm;
(20) the coated granule of any of the above-mentioned (14) to (17), wherein the drug granule has a particle size of 0.3 mm–1 mm;
(21) the coated granule of any of the above-mentioned (14) to (17), wherein the drug granule has a particle size of 0.5 mm–0.9 mm;
(22) the coated granule of any of the above-mentioned (14) to (17), wherein the drug granule has a particle size of 0.1 mm–0.5 mm;
(23) the coated granule of any of the above-mentioned (14) to (17), wherein the drug granule has a particle size of 0.2 mm–0.4 mm;
(24) a capsule preparation comprising the coated granule of the above-mentioned (18), (19), (20) or (21);
(25) a tablet preparation comprising the coated granule of the above-mentioned (19), (22) or (23);
(26) the coated granule of the above-mentioned (14), wherein the water soluble drug is N,N-dimethylimidodicarbonimidicdiamide, N-butylimidodicarbonimidicdiamide, N-(2-phenylethyl) imidodicarbonimidicdiamide, (1-hydroxyethylidene) bis-phosphonate, (4-amino-1-hydroxybutylidene) bis-phosphonate, (dichloromethylene) bis-phosphonate, ascorbic acid, sodium ascorbate, ethosuximide, sodium valproate, phenytoin sodium, amitriptyline hydrochloride, imipramine hydrochloride, lithium citrate, caffeine citrate, amantadine hydrochloride, chlorpromazine hydrochloride, thioridazine hydrochloride, meclofenoxate hydrochloride, oxytetracycline hydrochloride, talampicillin hydrochloride, tetracycline hydrochloride, pivmecillinum hydrochloride, vancomycin hydrochloride, lincomycin hydrochloride, potassium clavulanate, cephradine, kanamycin sulfate, fradiomycin sulfate, cloxacillin sodium, dicloxacillin sodium, tolperisone hydrochloride, chloral hydrate, acebutolol hydrochloride, procainamide hydrochloride, mexiletine hydrochloride, trapidil, diethyl carbamazine citrate, potassium bromide, sodium bromide, tranexamic acid, sodium cromoglicate, antipyrine, sodium salicylate, tiaramide hydrochloride, sulpyrine, naproxen sodium, migrenin, isoniazid, potassium iodide, potassium chloride, calcium chloride, sodium chloride, ethylcysteine hydrochloride, procarbazine hydrochloride, ranitidine hydrochloride, penicillamine, penicillamine hydrochloride, flavoxate hydrochloride, hexamine mandelate, alprenolol hydrochloride, indenolol hydrochloride, oxprenolol hydrochloride, verapamil hydrochloride, flecainide acetate, metoprolol tartarate, diltiazem hydrochloride, propranolol hydrochloride, captopril, papaverine hydrochloride, phenobarbital sodium, clomipramine hydrochloride, diphenhydramine hydrochloride, hydroxyzine hydrochloride, promethazine hydrochloride, doxycycline hydrochloride, noscapine hydrochloride, hydrocotarnine hydrochloride, dl-methylephedrine hydrochloride, pentoxyverine citrate, orciprenaline sulfate, phenylpropanolamine hydrochloride, potassium guaiacolsulfonate, pyridoxine hydrochloride, fursultiamine hydrochloride, niacinamide, calcium pantothenate, pethidine hydrochloride, loxoprofen sodium, cyanamide, pyridostigmine bromide, iron II sulfide, or a pharmaceutically acceptable salt thereof;
(26') the coated granule of the above-mentioned (14), wherein the water soluble drug is N,N-dimethylimidodicarbonimidicdiamide, N-butylimidodicarbonimidicdiamide, N-(2-phenylethyl) imidodicarbonimidicdiamide, (1-hydroxyethylidene) bis-phosphonate, (4-amino-1-hydroxybutylidene) bis-phosphonate, (dichloromethylene) bis-phosphonate, ascorbic acid, sodium ascorbate, gabapentin, ethosuximide, sodium valproate, phenytoin sodium, amitriptyline hydrochloride, imipramine hydrochloride, lithium citrate, caffeine citrate, amantadine hydrochloride, chlorpromazine hydrochloride, thioridazine hydrochloride, meclofenoxate hydrochloride, oxytetracycline hydrochloride, talampicillin hydrochloride, tetracycline hydrochloride, pivmecillinum hydrochloride, vancomycin hydrochloride, lincomycin hydrochloride, potassium clavulanate, cephradine, kanamycin sulfate, fradiomycin sulfate, cloxacillin sodium, dicloxacillin sodium, ciprofloxacin hydrochloride, amoxicillin, tolperisone hydrochloride, chloral hydrate, acebutolol hydrochloride, procainamide hydrochloride, mexiletine hydrochloride, trapidil, diethyl carbamazine citrate, potassium bromide, sodium bromide, tranexamic acid, sodium cromoglicate, antipyrine, sodium salicylate, tiaramide hydrochloride, sulpyrine, naproxen sodium, migrenin, isoniazid, potassium iodide, potassium chloride, calcium chloride, sodium chloride, ethylcysteine hydrochloride, procarbazine hydrochloride, cimetidine, ranitidine hydrochloride, penicillamine, penicillamine hydrochloride, flavoxate hydrochloride, hexamine mandelate, alprenolol hydrochloride, indenolol hydrochloride, oxprenolol hydrochloride, verapamil hydrochloride, flecainide acetate, metoprolol tartarate, diltiazem hydrochloride, propranolol hydrochloride, captopril, papaverine hydrochloride, phenobarbital sodium, clomipramine hydrochloride, diphenhydramine hydrochloride, hydroxyzine hydrochloride, promethazine hydrochloride, doxycycline hydrochloride, noscapine hydrochloride, hydrocotarnine hydrochloride, dl-methylephedrine hydrochloride, pentoxyverine citrate, orciprenaline sulfate, phenylpropanolamine hydrochloride, carbocysteine, potassium guaiacolsulfonate, pyridoxine hydrochloride, fursultiamine hydrochloride, niacinamide, calcium pantothenate, pethidine hydrochloride, loxoprofen sodium, cyanamide, pyridostigmine bromide, iron II sulfide, or a pharmaceutically acceptable salt thereof;
(27) the coated granule of the above-mentioned (14), wherein the water soluble drug is N,N-dimethylimidodicarbonimidicdiamide, N-butylimidodicarbonimidicdiamide, N-(2-phenylethyl) imidodicarbonimidicdiamide, (1-hydroxyethylidene) bis-phosphonate, (4-amino-1-hydroxybutylidene) bis-phosphonate, (dichloromethylene) bis-phosphonate, ascorbic acid, sodium ascorbate, ethosuximide, sodium valproate, phenytoin sodium, amitriptyline hydrochloride, imipramine hydrochloride, lithium citrate, caffeine citrate, amantadine hydrochloride, chlorpromazine hydrochloride, thioridazine hydrochloride, meclofenoxate hydrochloride, oxytetracycline hydrochloride, talampicillin hydrochloride, tetracycline hydrochloride, pivmecillinum hydrochloride, vancomycin hydrochloride, lincomycin hydrochloride, potassium clavulanate, cephradine, kanamycin sulfate, fradiomycin sulfate, cloxacillin sodium, dicloxacillin sodium, tolperisone hydrochloride, chloral hydrate, acebutolol hydrochloride, procainamide hydrochloride, mexiletine hydrochloride, trapidil, diethyl carbamazine citrate, potassium bromide, sodium bromide, tranexamic acid, sodium cromoglicate, antipyrine, sodium salicylate, tiaramide hydrochloride, sulpyrine, naproxen sodium, migrenin, isoniazid, potassium iodide, potassium chloride, calcium chloride, sodium chloride, ethylcysteine hydrochloride, procarbazine hydrochloride, ranitidine hydrochloride, penicillamine, penicillamine hydrochloride, flavoxate hydrochloride, hexamine mandelate, or a pharmaceutically acceptable salt thereof;

(27') the coated granule of the above-mentioned (14), wherein the water soluble drug is N,N-dimethylimidodicarbonimidicdiamide, N-butylimidodicarbonimidicdiamide, N-(2-phenylethyl) imidodicarbonimidicdiamide, (1-hydroxyethylidene) bis-phosphonate, (4-amino-1-hydroxybutylidene) bis-phosphonate, (dichloromethylene) bis-phosphonate, ascorbic acid, sodium ascorbate, gabapentin, ethosuximide, sodium valproate, phenytoin sodium, amitriptyline hydrochloride, imipramine hydrochloride, lithium citrate, caffeine citrate, amantadine hydrochloride, chlorpromazine hydrochloride, thioridazine hydrochloride, meclofenoxate hydrochloride, oxytetracycline hydrochloride, talampicillin hydrochloride, tetracycline hydrochloride, pivmecillinum hydrochloride, vancomycin hydrochloride, lincomycin hydrochloride, potassium clavulanate, cephradine, kanamycin sulfate, fradiomycin sulfate, cloxacillin sodium, dicloxacillin sodium, ciprofloxacin hydrochloride, amoxicillin, tolperisone hydrochloride, chloral hydrate, acebutolol hydrochloride, procainamide hydrochloride, mexiletine hydrochloride, trapidil, diethyl carbamazine citrate, potassium bromide, sodium bromide, tranexamic acid, sodium cromoglicate, antipyrine, sodium salicylate, tiaramide hydrochloride, sulpyrine, naproxen sodium, migrenin, isoniazid, potassium iodide, potassium chloride, calcium chloride, sodium chloride, ethylcysteine hydrochloride, procarbazine hydrochloride, cimetidine, ranitidine hydrochloride, penicillamine, penicillamine hydrochloride, flavoxate hydrochloride, hexamine mandelate, carbocisteine, or a pharmaceutically acceptable salt thereof;

(28) the coated granule of the above-mentioned (14), wherein the water soluble drug is N,N-dimethylimidodicarbonimidicdiamide, N-butylimidodicarbonimidicdiamide or a pharmaceutically acceptable salt thereof;

(28') the coated granule of the above-mentioned (14), wherein the water soluble drug is N,N-dimethylimidodicarbonimidicdiamide, N-butylimidodicarbonimidicdiamide, N-(2-phenylethyl) imidodicarbonimidicdiamide, (1-hydroxyethylidene) bis-phosphonate, (4-amino-1-hydroxybutylidene) bis-phosphonate, (dichloromethylene) bis-phosphonate, gabapentin, ciprofloxacin hydrochloride, sodium valproate, potassium clavulanate, amoxicillin, mexiletine hydrochloride, tranexamic acid, carbocisteine, loxoprofen sodium, ranitidine hydrochloride, or a pharmaceutically acceptable salt thereof;

(29) the coated granule of any of the above-mentioned (14)–(24) and (26)–(28), wherein one or more than one sustained release film coating agent is selected from the group consisting of a water insoluble cellulose derivative, a water insoluble vinyl derivative, a water insoluble acrylic polymer and a wax;

(30) the coated granule of any of the above-mentioned (14)–(24) and (26)–(28), wherein one or more than one sustained release film coating agent is selected from the group consisting of ethylcellulose, cellulose acetate, polyvinyl acetate, polyvinyl chloride, ethyl acrylate-methyl methacrylate copolymer, aminoalkyl methacrylate copolymer RS, dimethylaminoethyl methacrylate-methyl methacrylate copolymer, methacrylic copolymer L, methacrylic copolymer S, glycerin fatty acid ester, paraffin, and hydroxypropylmethyl cellulose acetate succinate;

(31) the coated granule of any of the above-mentioned (14)–(24) and (26)–(28), wherein one or more than one sustained release film coating agent is selected from the group consisting of AQUA Coat (registered trademark; Asahi Chemical Industry Co., LTD.), Eudragit RS30D (registered trademark; ROHM CO. LTD.), Eudragit NE30D (registered trademark; ROHM CO. LTD.), Eudragit RL30D (registered trademark; ROHM CO. LTD.), Ethocel (registered trademark; The Dow Chemical Company), DAC (registered trademark; Eastman Kodak Company), AQOAT HF (registered trademark; Shin-Etsu Chemical Co., Ltd.), AQOAT HG (registered trademark; Shin-Etsu Chemical Co., Ltd.), Eudragit RS100 (registered trademark; ROHM CO. LTD.) and Eudragit RL100 (registered trademark; ROHM CO. LTD.);

(32) the coated granule of any of the above-mentioned (14)–(24) and (26)–(28), wherein the sustained release film coating agent is contained in an amount of 5% (W/W)–100% (W/W) of the drug granule;

(33) the coated granule of any of the above-mentioned (14)–(24) and (26)–(28), wherein the sustained release film coating agent is contained in an amount of 10% (W/W)–50% (W/W) of the drug granule;

(34) the coated granule of any of the above-mentioned (14)–(24) and (26)–(28), wherein the sustained release film coating agent is contained in an amount of 10% (W/W)–35% (W/W) of the drug granule;

(35) an oral tablet preparation obtained or obtainable by tableting a component comprising a lubricant and a coated granule obtained or obtainable by coating, with a sustained release film coating agent, a drug granule obtained or obtainable by a method including a granulation step of spraying a solution of a water soluble drug on a crystal of said water soluble drug;

(35') the oral tablet preparation of the above-mentioned (35), wherein the solution of the water soluble drug is sprayed substantially without using a binder or in the absence of a binder, and wherein the drug granule has a granular strength of 650–2500 gf/mm$^2$;

(36) an oral tablet preparation obtained or obtainable by tableting a component comprising a lubricant, an excipient and a coated granule obtained or obtainable by coating, with a sustained release film coating agent, drug granules obtained or obtainable by a method comprising a granulation step of spraying a solution of a water soluble drug on a crystal of said water soluble drug;

(36') the oral tablet preparation of the above-mentioned (36), wherein the solution of the water soluble drug is sprayed substantially without using a binder or in the absence of a binder, and wherein the drug granule has a granular strength of 650–2500 gf/mm$^2$;

(37) an oral tablet preparation obtained or obtainable by tableting a component comprising a lubricant, an excipient, a disintegrant and a coated granule obtained or obtainable by coating, with a sustained release coating agent, a drug granule obtained or obtainable by a method comprising a granulation step of spraying a solution of a water soluble drug on a crystal of said water soluble drug;

(37') the oral tablet preparation of the above-mentioned (37), wherein the solution of the water soluble drug is sprayed substantially without using a binder or in the absence of a binder, and wherein the drug granule has a granular strength of 650–2500 gf/mm$^2$;

(38) the oral tablet preparation of the above-mentioned (35), (36) or (37), which is tableted at a pressure of 5 kg–30 kg;

(39) a coated granule obtained or obtainable by coating, with an enteric coating agent, a drug granule obtained or obtainable by a method comprising a granulation step of spraying a solution of a water soluble drug on a crystal of said water soluble drug;

(39') the coated granule of the above-mentioned (39), wherein the solution of the water soluble drug is sprayed substantially without using a binder or in the absence of a binder, and wherein the drug granule has a granular strength of 650–2500 gf/mm$^2$;

(40) the coated granule of the above-mentioned (39), wherein the water soluble drug has an aqueous solubility of not less than 5% (W/W);

(41) the coated granule of the above-mentioned (39), wherein the water soluble drug has an aqueous solubility of not less than 10% (W/W);

(42) the coated granule of the above-mentioned (39), wherein the water soluble drug has an aqueous solubility of not less than 20% (W/W);

(43) the coated granule of any of the above-mentioned (39) to (42), wherein the drug granule has a particle size of 0.05 mm–1.5 mm;

(44) the coated granule of any of the above-mentioned (39) to (42), wherein the drug granule has a particle size of 0.1 mm–1 mm;

(45) the coated granule of any of the above-mentioned (39) to (42), wherein the drug granule has a particle size of 0.3 mm–1 mm;

(46) the coated granule of any of the above-mentioned (39) to (42), wherein the drug granule has a particle size of 0.5 mm–0.9 mm;

(47) the coated granule of any of the above-mentioned (39) to (42), wherein the drug granule has a particle size of 0.1 mm–0.5 mm;

(48) the coated granule of any of the above-mentioned (39) to (42), wherein the drug granule has a particle size of 0.2 mm–0.4 mm;

(49) a capsule preparation comprising the coated granule of the above-mentioned (43), (44), (45) or (46).

(50) a tablet preparation comprising the coated granule of the above-mentioned (44), (47) or (48).

(51) the coated granule of the above-mentioned (39), wherein the water soluble drug is N,N-dimethylimidodicarbonimidicdiamide, N-butylimidodicarbonimidicdiamide, N-(2-phenylethyl) imidodicarbonimidicdiamide, (1-hydroxyethylidene) bis-phosphonate, (4-amino-1-hydroxybutylidene) bis-phosphonate, (dichloromethylene) bis-phosphonate, ascorbic acid, sodium ascorbate, ethosuximide, sodium valproate, phenytoin sodium, amitriptyline hydrochloride, imipramine hydrochloride, lithium citrate, caffeine citrate, amantadine hydrochloride, chlorpromazine hydrochloride, thioridazine hydrochloride, meclofenoxate hydrochloride, oxytetracycline hydrochloride, talampicillin hydrochloride, tetracycline hydrochloride, pivmecillinum hydrochloride, vancomycin hydrochloride, lincomycin hydrochloride, potassium clavulanate, cephradine, kanamycin sulfate, fradiomycin sulfate, cloxacillin sodium, dicloxacillin sodium, tolperisone hydrochloride, chloral hydrate, acebutolol hydrochloride, procainamide hydrochloride, mexiletine hydrochloride, trapidil, diethyl carbamazine citrate, potassium bromide, sodium bromide, tranexamic acid, sodium cromoglicate, antipyrine, sodium salicylate, tiaramide hydrochloride, sulpyrine, naproxen sodium, migrenin, isoniazid, potassium iodide, potassium chloride, calcium chloride, sodium chloride, ethylcysteine hydrochloride, procarbazine hydrochloride, ranitidine hydrochloride, penicillamine, penicillamine hydrochloride, flavoxate hydrochloride, hexamine mandelate, alprenolol hydrochloride, indenolol hydrochloride, oxprenolol hydrochloride, verapamil hydrochloride, flecainide acetate, metoprolol tartarate, diltiazem hydrochloride, propranolol hydrochloride, captopril, papaverine hydrochloride, phenobarbital sodium, clomipramine hydrochloride, diphenhydramine hydrochloride, hydroxyzine hydrochloride, promethazine hydrochloride, doxycycline hydrochloride, noscapine hydrochloride, hydrocotarnine hydrochloride, dl-methylephedrine hydrochloride, pentoxyverine citrate, orciprenaline sulfate, phenylpropanolamine hydrochloride, potassium guaiacolsulfonate, pyridoxine hydrochloride, fursultiamine hydrochloride, niacinamide, calcium pantothenate, pethidine hydrochloride, loxoprofen sodium, cyanamide, pyridostigmine bromide, iron II sulfide, or a pharmaceutically acceptable salt thereof;

(51') the coated granules of the above-mentioned (39), wherein the water soluble drug is N,N-dimethylimidodicarbonimidicdiamide, N-butylimidodicarbonimidicdiamide, N-(2-phenylethyl) imidodicarbonimidicdiamide, (1-hydroxyethylidene) bis-phosphonate, (4-amino-1-hydroxybutylidene) bis-phosphonate, (dichloromethylene) bis-phosphonate, ascorbic acid, sodium ascorbate, gabapentin, ethosuximide, sodium valproate, phenytoin sodium, amitriptyline hydrochloride, imipramine hydrochloride, lithium citrate, caffeine citrate, amantadine hydrochloride, chlorpromazine hydrochloride, thioridazine hydrochloride, meclofenoxate hydrochloride, oxytetracycline hydrochloride, talampicillin hydrochloride, tetracycline hydrochloride, pivmecillinum hydrochloride, vancomycin hydrochloride, lincomycin hydrochloride, potassium clavulanate, cephradine, kanamycin sulfate, fradiomycin sulfate, cloxacillin sodium, dicloxacillin sodium, ciprofloxacin hydrochloride, amoxicillin, tolperisone hydrochloride, chloral hydrate, acebutolol hydrochloride, procainamide hydrochloride, mexiletine hydrochloride, trapidil, diethyl carbamazine citrate, potassium bromide, sodium bromide, tranexamic acid, sodium cromoglicate, antipyrine, sodium salicylate, tiaramide hydrochloride, sulpyrine, naproxen sodium, migrenin, isoniazid, potassium iodide, potassium chloride, calcium chloride, sodium chloride, ethylcysteine hydrochloride, procarbazine hydrochloride, cimetidine, ranitidine hydrochloride, penicillamine, penicillamine hydrochloride, flavoxate hydrochloride, hexamine mandelate, carbocysteine, alprenolol hydrochloride, indenolol hydrochloride, oxprenolol hydrochloride, verapamil hydrochloride, flecainide acetate, metoprolol tartarate, diltiazem hydrochloride, propranolol hydrochloride, captopril, papaverine hydrochloride, phenobarbital sodium, clomipramine hydrochloride, diphenhydramine hydrochloride, hydroxyzine hydrochloride, promethazine hydrochloride, doxycycline hydrochloride, noscapine hydrochloride, hydrocotarnine hydrochloride, dl-methylephedrine hydrochloride, pentoxyverine citrate, orciprenaline sulfate, phenylpropanolamine hydrochloride, potassium guaiacolsulfonate, pyridoxine hydrochloride, fursultiamine hydrochloride, niacinamide, calcium pantothenate, pethidine hydrochloride, loxoprofen sodium, cyanamide, pyridostigmine bromide, iron II sulfide, or a pharmaceutically acceptable salt thereof;

(52) the coated granule of the above-mentioned (39), wherein the water soluble drug is N,N-dimethylimidodicarbonimidicdiamide, N-butylimidodicarbonimidicdiamide, N-(2-phenylethyl) imidodicarbonimidicdiamide, (1-hydroxyethylidene) bis-phosphonate, (4-amino-1-hydroxybutylidene) bis-phosphonate, (dichloromethylene) bis-phosphonate, ascorbic acid, sodium ascorbate, ethosuximide, sodium valproate, phenytoin sodium, amitriptyline hydrochloride, imipramine hydrochloride, lithium citrate, caffeine citrate, amantadine hydrochloride, chlorpromazine hydrochloride, thioridazine hydrochloride, meclofenoxate hydrochloride, oxytetracycline hydrochloride, talampicillin hydrochloride, tetracycline hydrochloride, pivmecillinum hydrochloride, vancomycin hydrochloride, lincomycin hydrochloride, potassium clavulanate, cephradine, kanamycin sulfate, fradiomycin sulfate, cloxacillin sodium, dicloxacillin sodium, tolperisone hydrochloride, chloral hydrate, acebutolol hydrochloride, procainamide hydrochloride, mexiletine hydrochloride, trapidil, diethyl carbamazine citrate, potassium bromide, sodium bromide, tranexamic acid, sodium cromoglicate, antipyrine, sodium salicylate, tiaramide hydrochloride, sulpyrine, naproxen sodium, migrenin, isoniazid, potassium iodide, potassium chloride, calcium chloride, sodium chloride, ethylcysteine hydrochloride, procarbazine hydrochloride, ranitidine hydrochloride, penicillamine, penicillamine hydrochloride, flavoxate hydrochloride, hexamine mandelate, or a pharmaceutically acceptable salt thereof;

(52') the coated granule of the above-mentioned (39), wherein the water soluble drug is N,N-dimethylimidodicarbonimidicdiamide, N-butylimidodicarbonimidicdiamide, N-(2-phenylethyl) imidodicarbonimidicdiamide, (1-hydroxyethylidene) bis-phosphonate, (4-amino-1-hydroxybutylidene) bis-phosphonate, (dichloromethylene) bis-phosphonate, ascorbic acid, sodium ascorbate, gabapentin, ethosuximide, sodium valproate, phenytoin sodium, amitriptyline hydrochloride, imipramine hydrochloride, lithium citrate, caffeine citrate, amantadine hydrochloride, chlorpromazine hydrochloride, thioridazine hydrochloride, meclofenoxate hydrochloride, oxytetracycline hydrochloride, talampicillin hydrochloride, tetracycline hydrochloride, pivmecillinum hydrochloride, vancomycin hydrochloride, lincomycin hydrochloride, potassium clavulanate, cephradine, kanamycin sulfate, fradiomycin sulfate, cloxacillin sodium, dicloxacillin sodium, ciprofloxacin hydrochloride, amoxicillin, tolperisone hydrochloride, chloral hydrate, acebutolol hydrochloride, procainamide hydrochloride, mexiletine hydrochloride, trapidil, diethyl carbamazine citrate, potassium bromide, sodium bromide, tranexamic acid, sodium cromoglicate, antipyrine, sodium salicylate, tiaramide hydrochloride, sulpyrine, naproxen sodium, migrenin, isoniazid, potassium iodide, potassium chloride, calcium chloride, sodium chloride, ethylcysteine hydrochloride, procarbazine hydrochloride, cimetidine, ranitidine hydrochloride, penicillamine, penicillamine hydrochloride, flavoxate hydrochloride, hexamine mandelate, carbocisteine or a pharmaceutically acceptable salt thereof;

(53) the coated granule of the above-mentioned (39), wherein the water soluble drug is N,N-dimethylimidodicarbonimidicdiamide, N-butylimidodicarbonimidicdiamide or a pharmaceutically acceptable salt thereof;

(53') the coated granule of the above-mentioned (39), wherein the water soluble drug is N,N-dimethylimidodicarbonimidicdiamide, N-butylimidodicarbonimidicdiamide, N-(2-phenylethyl) imidodicarbonimidicdiamide, (1-hydroxyethylidene) bis-phosphonate, (4-amino-1-hydroxybutylidene) bis-phosphonate, (dichloromethylene) bis-phosphonate, gabapentin, ciprofloxacin hydrochloride, sodium valproate, potassium clavulanate, amoxicillin, mexiletine hydrochloride, tranexamic acid, carbocisteine, loxoprofen sodium, ranitidine hydrochloride, or a pharmaceutically acceptable salt thereof;

(54) the coated granule of any of the above-mentioned (39)–(49) and (51)–(53), wherein one or more than one enteric coating agent is selected from the group consisting of an enteric coating cellulose derivative, an enteric coating vinyl derivative, an enteric coating acrylic polymer, shellac and a wax;

(55) the coated granule of any of the above-mentioned (39)–(49) and (51)–(53), wherein one or more than one enteric coating agent is selected from the group consisting of cellulose acetate phthalate, cellulose acetate tetrahydrophthalate, hydroxypropylmethylcellulose phthalate, hydroxypropylmethylcellulose acetate succinate, carboxymethylethylcellulose, hydroxyethylethylcellulose phthalate, polyvinylacetate phthalate, methacrylic copolymer L, methacrylic copolymer LD, methacrylic copolymer S and corn protein;

(56) the coated granule of any of the above-mentioned (39)–(49) and (51)–(53), wherein one or more than one enteric coating agent is selected from the group consisting of CAP (registered trademark; Eastman Kodak Company), HPMCP HP-55 (registered trademark; Shin-Etsu Chemical Co., Ltd.), HPMCP HP-50 (registered trademark; Shin-Etsu Chemical Co., Ltd.), AQOAT LG (registered trademark; Shin-Etsu Chemical Co., Ltd.), AQOAT MG (registered trademark; Shin-Etsu Chemical Co., Ltd.), AQOAT LF (registered trademark; Shin-Etsu Chemical Co., Ltd.), AQOAT MF (registered trademark; Shin-Etsu Chemical Co., Ltd.), CMEC OS (registered trademark; FREUND Inc.), Eudragit L100 (registered trademark; ROHM CO. LTD.), Eudragit L100-55 (registered trademark; ROHM CO. LTD.), Eudragit L30D-55 (registered trademark; ROHM CO. LTD.), Eudragit S100 (registered trademark; ROHM CO. LTD.), and Zein DP (registered trademark; Showa Sangyo Co., Ltd.);

(57) the coated granule of any of the above-mentioned (39)–(49) and (51)–(53), wherein the enteric coating agent is contained in an amount of 5% (W/W)–100% (W/W) of the drug granule;

(58) the coated granule of any of the above-mentioned (39)–(49) and (51)–(53), wherein the enteric coating agent is contained in an amount of 10% (W/W)–50% (W/W) of the drug granule;

(59) the coated granule of any of the above-mentioned (39)–(49) and (51)–(53), wherein the enteric coating agent is contained in an amount of 20% (W/W)–40% (W/W) of the drug granule;

(60) an oral tablet preparation obtained or obtainable by tableting a component comprising a lubricant and a coated granule obtained or obtainable by coating, with an enteric coating agent, a drug granule obtained or obtainable by a method comprising a granulation step of spraying a solution of a water soluble drug on a crystal of said water soluble drug;

(60') the oral tablet preparation of the above-mentioned (60), wherein the coated granule is obtained or obtainable by coating, with an enteric coating agent, a drug granule obtained or obtainable by a method comprising a granulation step of spraying only a solution of a water soluble drug on a crystal of said water soluble drug, substantially without using a binder or in the absence of a binder, and wherein the drug granule has a granular strength of 650–2500 gf/mm$^2$;

(61) an oral tablet preparation obtained or obtainable by tableting a component comprising a lubricant, an excipient and a coated granule obtained or obtainable by coating, with an enteric coating agent, a drug granule obtained or obtainable by a method comprising a granulation step of spraying a solution of a water soluble drug on a crystal of said water soluble drug;

(61') the oral tablet preparation of the above-mentioned (61), wherein the coated granule is obtained or obtainable by coating, with an enteric coating agent, a drug granule obtained or obtainable by a method comprising a granulation step of spraying only a solution of a water soluble drug on a crystal of said water soluble drug, substantially without using a binder or in the absence of a binder, and wherein the drug granule has a granular strength of 650–2500 gf/mm²;

(62) an oral tablet preparation obtained or obtainable by tableting a component comprising a lubricant, an excipient, a disintegrant and a coated granule obtained or obtainable by coating, with an enteric coating agent, a drug granule obtained or obtainable by a method comprising a granulation step of spraying a solution of a water soluble drug on a crystal of said water soluble drug;

(62') the oral tablet preparation of the above-mentioned (62), wherein the coated granule is obtained or obtainable by coating, with an enteric coating agent, a drug granule obtained or obtainable by a method comprising a granulation step of spraying only a solution of a water soluble drug on a crystal of said water soluble drug, substantially without using a binder or in the absence of a binder, and wherein the drug granule has a granular strength of 650–2500 gf/mm²;

(63) the oral tablet preparation of the above-mentioned (60), (61) or (62), which is tableted at a pressure of 5 kg–30 kg;

(64) a pharmaceutical preparation comprising a drug granule described in any of the above-mentioned (1)–(13) and a pharmaceutically acceptable additive;

(65) a pharmaceutical preparation comprising a coated granule described in any of the above-mentioned (14)–(34) and (39)–(59) and a pharmaceutically acceptable additive;

(66) a method of manufacturing a drug granule, which comprises a granulation step of spraying a solution of a water soluble drug on a crystal of said water soluble drug;

(66') the method according to the above-mentioned (66), wherein the drug granule is obtained or obtainable by a method comprising a granulation step of spraying only a solution of a water soluble drug on a crystal of said water soluble drug, substantially without using a binder or in the absence of a binder, and wherein the drug granule has a granular strength of 650–2500 gf/mm²;

(67) the method according to the above-mentioned (66), wherein the amount of water solude drug in the solution sprayed is in a 2-fold to 3000-fold amount of a crystal of the water soluble drug;

(68) the method according to the above-mentioned (66) or (67), wherein the concentration of the water soluble drug solution is from 5% (W/W) to 50% (W/W);

(69) the method according to the above-mentioned (68), wherein the concentration of the water soluble drug solution is from 10% (W/W) to 50% (W/W);

(70) the method according to the above-mentioned (68), wherein the concentration of the water soluble drug solution is from 20% (W/W) to 50% (W/W);

(71) a method of manufacturing a coated granule, which comprises a granulation step of spraying a solution of a water soluble drug on a crystal of said water soluble drug, and a step of coating the drug granule with a release control film coating agent;

(71') the method according to the above-mentioned (71), wherein the drug granule is obtained or obtainable by a method comprising a granulation step of spraying only a solution of a water soluble drug on a crystal of said water soluble drug, substantially without using a binder or in the absence of a binder, and wherein the drug granule has a granular strength of 650–2500 gf/mm²;

(72) a water soluble drug granule substantially free of a binder and having a granular strength of 650–2500 gf/mm², comprising a water soluble drug crystal as a nucleus.

(73) the drug granules of the above-mentioned (72), wherein the water soluble drug has an aqueous solubility of not less than 5% (W/W);

(74) the drug granule of the above-mentioned (72), wherein the water soluble drug has an aqueous solubility of not less than 10% (W/W);

(75) the drug granule of the above-mentioned (72), wherein the water soluble drug has an aqueous solubility of not less than 20% (W/W);

(76) the drug granule of any of the above-mentioned (72) to (75), wherein the granule has a particle size of 0.05 mm–1.5 mm;

(77) the drug granule of any of the above-mentioned (72) to (75), wherein the granule has a particle size of 0.1 mm–1 mm;

(78) the drug granule of any of the above-mentioned (72) to (75), wherein the granule has a particle size of 0.3 mm–1 mm;

(79) the drug granule of any of the above-mentioned (72) to (75), wherein the granule has a particle size of 0.5 mm–0.9 mm;

(80) the drug granule of any of the above-mentioned (72) to (75), wherein the granule has a particle size of 0.1 mm–0.5 mm;

(81) the drug granule of any of the above-mentioned (72) to (75), wherein the granule has a particle size of 0.2 mm–0.4 mm;

(82) a coated granule comprising drug granule of any of the above-mentioned (72)–(81) and a release control film coating agent applied thereon;

(83) a coated granule comprising an inner layer comprising a drug granule of any of the above-mentioned (72)–(81) and an outer layer comprising a release control film coating agent; and the like.

DETAILED DESCRIPTION OF THE INVENTION

Figure 1:
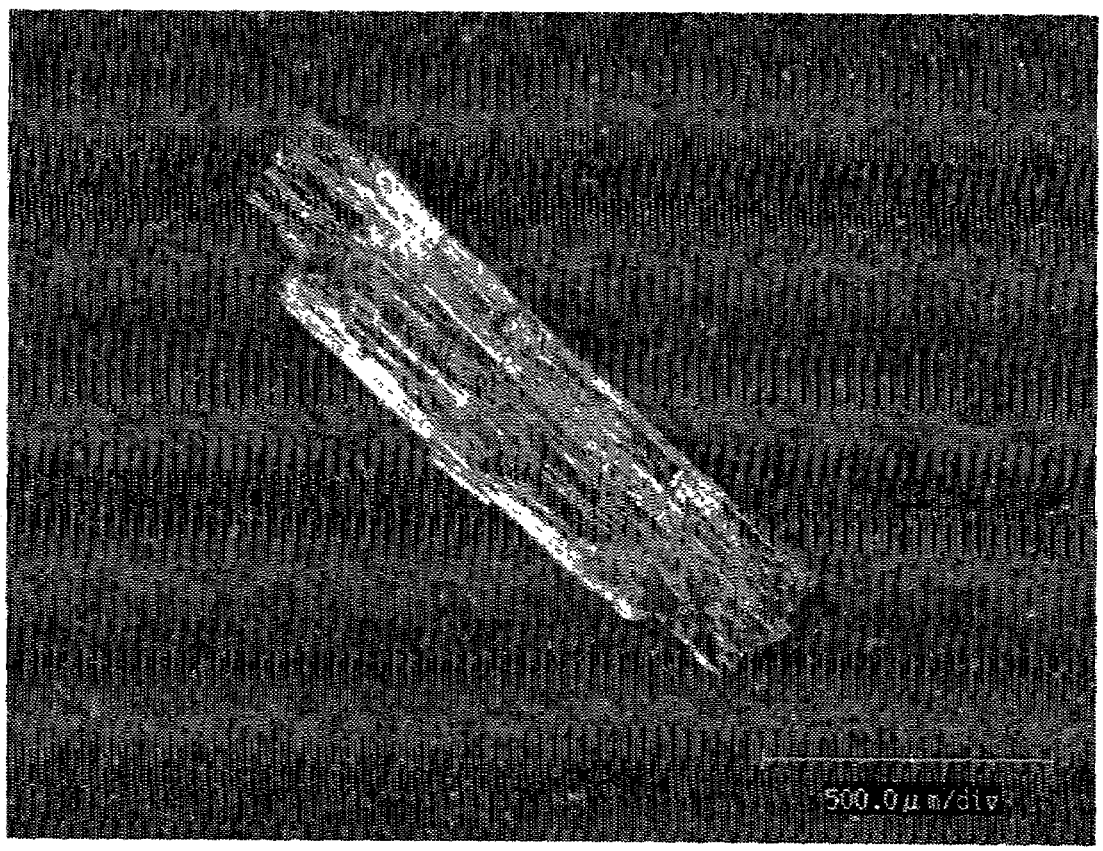
FIG. 1 is a photograph showing the single crystal of metformin hydrochloride used as a drug nucleus in Examples 1–3.

The present invention is explained in detail in the following.

The present invention provides a production method of drug granules containing a water soluble drug as a main component, comprising granulation step of spraying a solution of the water soluble to a crystal of said water soluble drug, to form the drug granules. The present invention also provides a drug granule having a granular strength of 650–2500 gf/mm², by granulation step of spraying only a solution of a water soluble drug on a crystal of the water soluble drug, substantially without using a binder or in the absence of a binder.

In the present invention, the "water soluble drug" includes a crystalline drug for pharmaceutical use, preferably a crystalline drug for oral administration. In the present specification, by the "water soluble" is meant an aqueous solubility of not less than 5% (W/W) at 25° C. The water soluble drug in the present invention preferably has an aqueous solubility of not less than 10% (W/W) at 25° C., more preferably not less than 20% (W/W) at 25° C. and particularly preferably not less than 30% (W/W) at 25° C. In the present invention, moreover, the "aqueous solubility" includes solubility in a pH buffer solution. For example, a buffer having a stable pH range can be used for a water soluble drug which is instable in a specific pH range. Furthermore, a pH buffering solution can be determined to increase the solubility. It is also possible to select basic conditions for a water soluble drug having an acidic residue and acidic conditions for a water soluble drug having a basic residue. An example of buffer includes phosphoric acid buffer, citrate buffer, boric acid buffer, glycine buffer and the like.

Specific examples of such water soluble drug include N,N-dimethylimidodicarbonimidicdiamide (metformin) (therapeutic agent of diabetes), N-butylimidodicarbonimidicdiamide (therapeutic agent of diabetes), N-(2-phenylethyl) imidodicarbonimidicdiamide (therapeutic agent of diabetes), (1-hydroxyethylidene) bis-phosphonate (ethydronic acid) (therapeutic agent of osteoporosis), (4-amino-1-hydroxybutylidene) bis-phosphonate (therapeutic agent of osteoporosis), (dichloromethylene) bis-phosphonate (therapeutic agent of osteoporosis), ascorbic acid (viatamin), sodium ascorbate (viatamin), gabapentin (antiepileptic agent), ethosuximide (antiepileptic agent), sodium valproate (antiepileptic agent), phenytoin sodium (antiepileptic agent), amitriptyline hydrochloride (antidepressant), imipramine hydrochloride (anti-depressant), lithium citrate (anti-depressant), caffeine citrate (analeptic), amantadine hydrochloride (anti-Parkinson's syndrome), chlorpromazine hydrochloride (antipsychotic agent), thioridazine hydrochloride (antipsychotic agent), meclofenoxate hydrochloride (anti-dizziness), oxytetracycline hydrochloride (antibiotics), talampicillin hydrochloride (antibiotics), tetracycline hydrochloride (antibiotics), pivmecillinum hydrochloride (antibiotics), vancomycin hydrochloride (antibiotics), lincomycin hydrochloride (antibiotics), potassium clavulanate (antibiotics), cephradine (antibiotics), kanamycin sulfate (antibiotics), fradiomycin sulfate (antibiotics), cloxacillin sodium (antibiotics), dicloxacillin sodium (antibiotics), ciprofloxacin hydrochloride (antibiotics), amoxicillin (antibiotics), tolperisone hydrochloride (centrally acting muscle relaxant), chloral hydrate (sedative), acebutolol hydrochloride (antiarrhythmic agent), procainamide hydrochloride (antiarrhythmic agent), mexiletine hydrochloride (antiarrhythmic agent), trapidil (anti-hypertensive agent), diethylcarbamazine citrate (antiparasitic), potassium bromide (sedative), sodium bromide (sedative hypnotic), tranexamic acid (antiallergic agent), sodium cromoglicate (antiallergic agent), antipyrine (analgesic antipyretic, anti-inflammatory agent), sodium salicylate (analgesic antipyretic, anti-inflammatory agent), tiaramide hydrochloride (analgesic antipyretic, anti-inflammatory agent), sulpyrine (analgesic antipyretic, anti-inflammatory agent), naproxen sodium (analgesic antipyretic, anti-inflammatory agent), migrenin (analgesic antipyretic, anti-inflammatory agent), isoniazid (antituberculosis drug), potassium iodide (expectorant), potassium chloride (electrolyte supply), calcium chloride (electrolyte supply), sodium chloride (electrolyte supply), ethylcysteine hydrochloride (expectorant), procarbazine hydrochloride (antimalignant agent), cimetidine (anti-ulcer agent), ranitidine hydrochloride (anti-ulcer agent), penicillamine (antirheumatic), penicillamine hydrochloride (antirheumatic), flavoxate hydrochloride (urologic agent), hexamine mandelate (urologic agent), alprenolol hydrochloride (antiarrhythmic agent), indenolol hydrochloride (antiarrhythmic agent), oxprenolol hydrochloride (antiarrhythmic agent), verapamil hydrochloride (antiarrhythmic agent), flecainide acetate (antiarrhythmic agent), metoprolol tartrate (antiarrhythmic agent), diltiazem hydrochloride (anti-hypertensive agent), propranolol hydrochloride (anti-hypertensive agent), captopril (anti-hypertensive agent), papaverine hydrochloride (anti-hypertensive agent), phenobarbital sodium (anti-convulsant), clomipramine hydrochloride (antidepressant), diphenhydramine hydrochloride (antihistamic agent), hydroxyzine hydrochloride (antihistamic agent), promethazine hydrochloride (antihistamic agent), doxycycline hydrochloride (antibiotics), noscapine hydrochloride (antitussive), hydrocotarnine hydrochloride (antitussive), dl-methylephedrine hydrochloride (antitussive), pentoxyverine citrate (antitussive), orciprenaline sulfate (antitussive), phenylpropanolamine hydrochloride (antitussive), carbocisteine (expectorant), potassium guaiacolsulfonate (expectorans), pyridoxine hydrochloride (vitamin), fursultiamine hydrochloride (vitamin), niacinamide (vitamin), calcium pantothenate (dysbolism improving agent), pethidine hydrochloride (analgesic antipyretic, anti-inflammatory agent), loxoprofen sodium (analgesic antipyretic, anti-inflammatory agent), cyanamide (alcoholphobics), pyridostigmine bromide (cholinesterase inhibitor), iron II sulfide (hematopoietics) and the like, and their pharmaceutically acceptable salts and the like.

Of the above-mentioned examples, preferable drug includes, N,N-dimethylimidodicarbonimidicdiamide, N-butylimidodicarbonimidicdiamide, N-(2-phenylethyl) imidodicarbonimidicdiamide, (1-hydroxyethylidene) bis-phosphonate, (4-amino-1-hydroxybutylidene) bis-phosphonate, (dichloromethylene) bis-phosphonate, ascorbic acid, sodium ascorbate, gabapentin, ethosuximide, sodium valproate, phenytoin sodium, amitriptyline hydrochloride, imipramine hydrochloride, lithium citrate, caffeine citrate, amantadine hydrochloride, chlorpromazine hydrochloride, thioridazine hydrochloride, meclofenoxate hydrochloride, oxytetracycline hydrochloride, talampicillin hydrochloride, tetracycline hydrochloride, pivmecillinum hydrochloride, vancomycin hydrochloride, lincomycin hydrochloride, potassium clavulanate, cephradine, kanamycin sulfate, fradiomycin sulfate, cloxacillin sodium, dicloxacillin sodium, ciprofloxacin hydrochloride, amoxicillin, tolperisone hydrochloride, chloral hydrate, acebutolol hydrochloride, procainamide hydrochloride, mexiletine hydrochloride, trapidil, diethyl carbamazine citrate, potassium bromide, sodium bromide, tranexamic acid, sodium cromoglicate, antipyrine, sodium salicylate, tiaramide hydrochloride, sulpyrine, naproxen sodium, migrenin, isoniazid, potassium iodide, potassium chloride, calcium chloride, sodium chloride, ethylcysteine hydrochloride, procarbazine hydrochloride, cimetidine, ranitidine hydrochloride, penicillamine, penicillamine hydrochloride, flavoxate hydrochloride, hexamine mandelate, carbocisteine and the like and their pharmaceutically acceptable salts and the like.

Of the above-mentioned examples, more preferable drugs include N,N-dimethylimidodicarbonimidicdiamide, N-butylimidodicarbonimidicdiamide, N-(2-phenylethyl) imidodicarbonimidicdiamide, (1-hydroxyethylidene) bis-phosphonate, (4-amino-1-hydroxybutylidene) bis-phosphonate, (dichloromethylene) bis-phosphonate, gabapentin, ciprofloxacin hydrochloride, sodium valproate, potassium clavulanate, amoxicillin, mexiletine hydrochloride, tranexamic acid, carbocisteine, loxoprofen sodium, ranitidine hydrochloride and the like and their pharmaceutically acceptable salts and the like.

As a pharmaceutically acceptable salt, exemplified when the water soluble drug has a basic substituent are salts with inorganic acid (e.g., hydrochloric acid, hydrobromic acid, nitric acid, sulfuric acid, phosphoric acid etc.) and salts with organic acid (e.g., formic acid, acetic acid, trifluoroacetic acid, propionic acid, lactic acid, tartaric acid, oxalic acid, fumaric acid, maleic acid, citric acid, malonic acid, methanesulfonic acid etc.). In addition, when the water soluble drug has an acidic functional group, salts with basic amino acid such as arginine, lysin and the like, alkali metal salt such as sodium salt, potassium salt and the like, alkaline earth metal salt such as calcium salt, magnesium salt and the like, and the like are mentioned. The water soluble drug of the present invention encompasses solvates such as hydrates of the salts and the like.

In the present invention, the granular strength can be measured using a table-top material tester (EZ Test-20N, Shimadzu Corporation).

Measurement Method:

One drug granule of the present invention is placed on a sample table of the table-top material tester. Using an upper compression jig having a diameter of 5 mm, the granule is compressed in a compression mode at 0.5 mm/min and the maximum peak is taken as the strength. The measurement is repeated 10 times and averaged. The strength is divided by the sectional area of the granule and taken as the granular strength.

The granular strength is in the range of from 650 to 2500 gf/mm$^2$. Preferable range is 700–2000 gf/mm$^2$, more preferable range is 750–1800 gf/mm$^2$.

The water soluble drug and crystals of the water soluble drug that become nucleus are of the same, which is selected from the above-mentioned examples. The water soluble drug and crystal of the water soluble drug that become nucleus is may be commercially available or can be produced and purified according to conventionally known methods. For example, column chromatography, recrystallization and the like are used for purification. Examples of the solvent for recrystallization include water, alcohol solvents such as methanol, ethanol, 2-propanol and the like, ether solvents such as diethyl ether and the like, ester solvents such as ethyl acetate and the like, aromatic hydrocarbon solvents such as toluene and the like, ketone solvents such as acetone and the like, hydrocarbon solvents such as hexane and the like, and the like and mixed solvents thereof and the like.

Examples of the solvent for a solution of a water soluble drug include water, alcohol solvents such as methanol, ethanol, 2-propanol and the like and mixed solvents thereof. Of these, preferable solvent is water, particularly purified water.

The concentration of the solution of a water soluble drug is not particularly limited but it is preferably not less than 5% (W/W), more preferably 10% (W/W)–50% (W/W), most preferably 20% (W/W)–50% (W/W). In particular, a concentration that makes a water soluble drug dissolve near the solubility of the drug in the solvent is particularly preferable. When the concentration of the solution of the water soluble drug is less than 5% (W/W), granulation becomes undesirably longer time.

While the temperature at which a water soluble drug is dissolved in a solvent varies depending on the concentration, stability in the solution and the like of the water soluble drug. Specifically, it is selected from the range of 5° C.–50° C.

According to the production method of the present invention, the above-mentioned solution of a water soluble drug is sprayed on a crystal of the water soluble drug, using the crystal of the water soluble drug as nucleus for granulation. Alternatively, only the above-mentioned solution of the water soluble drug is sprayed on the crystal of the water soluble drug, substantially without using a binder or in the absence of a binder, using the obtained crystal of the water soluble drug as nuclei, and the crystal is granulated. The crystal of a water soluble drug used as the nucleus in the granulation step (hereinafter sometimes to be referred to as drug nucleus) are not particularly limited as to the shape, and those having various known shapes can be used. The drug nucleus may be single crystals or polycrystals of a water soluble drug. The size of the drug nucleus is not particularly limited. Example of a particle size measured through a sieve is 10 μm–1000 μm, preferably 20 μm–1000 μm, more preferably 50 μm–500 μm. When the drug nucleus has a particle size of less than 10 μm, granulation becomes difficult, when it is less than 20 μm, granulation conditions unpreferably becomes a narrower tolerance range, and when it exceeds 1000 μm, flowability during granulation becomes poor, and unpreferable.

In the present invention, by the "spraying only a solution of the water soluble drug" is meant that it does not include spraying a powder of the drug on the drug nucleus, combined with forming of wet spherical particles while spraying a liquid such as water and the like during the granulation step.

The amount of water soluble drug in the solution to be sprayed on the drug nucleus is preferably at least equivalent, more preferably 2-fold to 33000-fold amount, particularly preferably 2-fold to 1000-fold amount, to the drug nucleus. For example, a solution containing a water soluble drug in the same amount as the charged amount of the drug nucleus is sprayed, half of the obtained drug granules is charged again, and a solution containing the water soluble drug in the same amount as the charged amount is sprayed. In this case, the frequency of spraying and the ratio of the charged amount and the amount to be sprayed may be appropriately determined to obtain drug granules having a desired size. The entire amount of the obtained granules may be charged again or the obtained granules may be weighed out and charged again.

The drug granule obtained by the above-mentioned method of the present invention is obtained by granulation without using a core, which is a physiologically inactive substance, but by using crystals of a water soluble drug as a nucleus in the presence of a bonding substance (sometimes to be referred to in the present specification as a binder). Unlike drug granules obtained by conventional production method, therefore, a drug granule consisting of a water soluble drug alone without a bonding substance can be realized. Such drug granule contains a water soluble drug as an active ingredient at a high density. As a result, a pharmaceutical preparation superior in drug release control can be realized in a smaller size than conventional ones. Furthermore, the drug granules of the present invention have a higher flowability than single crystals of the drug. When they are prepared into capsule preparation or folded piece granule preparation, the content can be made constant and fine stability can be achieved.

The drug granules obtained in the present invention can be used as they are or may be used as a pharmaceutical preparation containing an additive acceptable for formulation of preparations. The above-mentioned pharmaceutical preparation includes, for example, a powder preparation, a fine granule preparation, a granule preparation, a tablet preparation, a capsule preparation, a troche preparation and the like. These may be coated as necessary depending on the object. In the present specification, by the "additive acceptable for formulation of preparations" is meant excipient, a film coating agent (coating agent), a coating aid, a coloring agent, a masking agent, a plasticizer, a lubricant, a disintegrant, a stabilizer, a sweetener, a corrigent, a binder, an antioxidant, a brightener, a flavoring agent, a flavor, a defoaming agent, a chewable preparation, a refrigerant, a sugar coating agent, a foaming agent, a disintegrating aid, a fluidizing agent and the like, that are conventionally and generally used in this field, depending on the form of a desired pharmaceutical preparation.

Examples of the binder include carmellose, carmellose sodium, copolyvidone, wheat starch, rice starch, corn starch, potato starch, hydroxyethylcellulose, hydroxypropylcellulose, hydroxypropylmethylcellulose 2208, hydroxypropylmethylcellulose 2906, hydroxypropylmethylcellulose 2910, pullulan, povidone, polyvinyl alcohol (fully hydrolyzed product), polyvinyl alcohol (partially hydrolyzed product) and the like.

In the present invention, by the "substantially without using a binder" is meant absence of use or use of only a small amount of a binder during granulation. By the "use of only a small amount of a binder" is specifically meant use of a binder in an amount of less than 1% (w/w) of the drug granule.

In the present invention, by the "in the absence of a binder" is meant without using a binder at all during granulation.

The drug granule of the present invention is subject to no particularly limitation as to shape, but from the aspect of the drug releaseability, a spherical shape having the smallest surface area is preferable. A shape having a long/short diameter ratio of not more than 1.2, apparent specific volume of aggregate of not more than 1.65 ml/g and an angle of repose of not more than 35 degrees is particularly preferable.

The "long/short diameter ratio" is a ratio of the length of the long axis to the length of short axis of the drug granule, which is obtained by placing drug granules at random on a slide glass for microscopes, photographing them, measuring the length of the longest axis (long diameter) and the length of short axis (short diameter), perpendicularly drawn from the middle point of the length of the long axis, of each of ten drug granules, and taking an average of the ratio of the long diameter to the short diameter of the ten drug granules.

The "specific volume" is determined by dropping particles having a weight "W" (ca. 30 g) gradually at a constant rate from right above of a 100 ml measuring cylinder and, after dropping, reading the volume of standing granules. That is, the specific volume is a value obtained by dividing volume "V" by weight "W" of the dropped particles and an average of 5 measures.

The "angle of repose" is an angle formed by a generatrix of a cone, which is formed by gently dropping drug granules on a horizontal plane, with the horizontal plane. To be specific, a cylindrical disc having a diameter of 5 cm is kept horizontally and granules are gradually dropped from about 1 cm above the center of the cylindrical disc at a constant rate. Since the granules form a bank, the point from which the granules are dropped is raised to keep about 1 cm from the top of the bank. When the cylindrical disc is entirely covered with the granules and a cone is formed with the granules, an angle formed by the upper part of the inclination formed by the granules with the horizontal plane (upper surface of the cylindrical disc) is read with a protractor on the periphery of the cylindrical disc. The measurement value is an average of two measures.

The particle size of the drug granules of the present invention is not particularly limited, but it is preferably in the range of 0.05 mm–1.5 mm, more preferably 0.1 mm–1 mm. When the particle size of the drug granules is less than 0.05 mm, the operability unpreferably tends to be poor, and when it exceeds 1.5 mm, easiness of taking medication and operability unpreferably tend to be poor. The particle size varies depending on the aqueous solubility, desired releaseability and the like of a water soluble drug, wherein more preferable range is determined depending on the form of a desired pharmaceutical preparation. For granule preparations or capsule preparations, for example, the particle size is preferably in the range of from 0.3 mm to 1 mm, particularly preferably 0.5 mm–0.9 mm. For tablet preparations, for example, the particle size is more preferably 0.1 mm–0.5 mm, particularly preferably 0.2 mm–0.4 mm. The particle size of the above-mentioned drug granules can be measured in the same manner as that of the aforementioned drug nucleus.

The drug granules of the present invention are preferably coated with a release control film coating agent to give coated granules, wherein the inner layer comprises the drug granule and the outer layer comprises the release control film coating agents. The release control film coating agent is not particularly limited and various conventionally known film coating agent can be used. For example, one or more selected from cellulose derivatives, vinyl derivatives, acrylic polymers, polyester polymers, urethane polymers, corn protein, shellac and wax can be used. Of the above-mentioned, preferred are one or more selected from water-soluble cellulose derivatives, water-soluble vinyl derivatives, water-soluble acrylic derivatives, water insoluble cellulose derivatives, water insoluble vinyl derivatives, water insoluble acrylic polymers, gastric coating vinyl derivatives, gastric coating acrylic polymers, enteric coating cellulose derivatives, enteric coating vinyl derivatives, enteric coating acrylic polymers, corn protein, shellac and wax. The release control film coating agent in the present invention is preferably a sustained release or an enteric film coating forming agent.

Examples of the sustained release film coating agent include one or more selected from water insoluble film coating agents, such as ethylcellulose, cellulose acetate, polyvinyl acetate, polyvinyl chloride, ethyl acrylate-methyl methacrylate copolymer, aminoalkyl methacrylate copolymer RS, dimethylaminoethyl methacrylate-methyl methacrylate copolymer, methacrylic copolymer L, methacrylic copolymer S, glycerin fatty acid ester, paraffin and hydroxypropylmethyl cellulose acetate succinate. Specific examples are one or more selected from AQUA Coat (registered trademark; Asahi Chemical Industry Co., Ltd.), Eudragit RS30D (registered trademark; ROHM CO. LTD.), Eudragit NE30D (registered trademark; ROHM CO. LTD.), Eudragit RL30D (registered trademark; ROHM CO. LTD.), Ethocel (registered trademark; The Dow Chemical Company), DAC (registered trademark; Eastman Kodak Company), AQOAT HF (registered trademark; Shin-Etsu Chemical Co., Ltd.), AQOAT HG (registered trademark; Shin-Etsu Chemical Co., Ltd.), Eudragit RS100 (registered trademark; ROHM CO. LTD.) and Eudragit RL100 (registered trademark; ROHM CO. LTD.). Of the above-mentioned examples, particularly preferred are one or more than one selected from AQUA Coat, Eudragit RS30D, Eudragit RL30D and Eudragit NE30D, because drug granules can be coated with a high concentration aqueous coating solution.

The enteric film coating agent is, for example, one or more selected from cellulose acetate phthalate, cellulose acetate tetrahydrophthalate, hydroxypropylmethylcellulose phthalate, hydroxypropylmethylcellulose acetate succinate, carboxymethylethylcellulose, hydroxyethylethylcellulose phthalate, polyvinyl acetate phthalate, methacrylic copolymer L, methacrylic copolymer LD, methacrylic copolymer S and corn protein. Specific examples include one or more selected from CAP (registered trademark; Eastman Kodak Company), HPMCP HP-55 (registered trademark; Shin-Etsu Chemical Co., Ltd.), HPMCP HP-50 (registered trademark; Shin-Etsu Chemical Co., Ltd.), AQOAT LG (registered trademark; Shin-Etsu Chemical Co., Ltd.), AQOAT MG (registered trademark; Shin-Etsu Chemical Co., Ltd.), AQOAT LF (registered trademark; Shin-Etsu Chemical Co., Ltd.), AQOAT MF (registered trademark; Shin-Etsu Chemical Co., Ltd.), CMEC OS (registered trademark; FREUND In c.), Eudragit L100 (registered trademark; ROHM CO. LTD.), Eudragit L100-55 (registered trademark; ROHM CO. LTD.), Eudragit L30D-55 (registered trademark; ROHM CO. LTD.), Eudragit S100 (registered trademark; ROHM CO. LTD.), and Zein DP (registered trademark; Showa Sangyo Co., Ltd.). Of the above-mentioned examples, particularly preferred are Eudragit L100-55, Eudragit L30D-55 and the like, because drug granules can be coated with a high concentration aqueous coating solution.

A solvent or dispersing solution for the release control film coating agent used in the present invention may be, for example, water, alcohol solvents such as methanol, ethanol, 2-propanol and the like and mixed solvents thereof. Particularly preferable solvent is water, particularly purified water.

In the present invention, the release control film coating agent may contain various additives such as coating aid, coloring agent, masking agent, plasticizer, lubricant and the like. Examples of the coating aid include hydrogenated oil, stearic acid, a salt thereof, glycerol monostearate, talc, kaolin, sucrose fatty acid ester, higher alcohol such as cetanol etc., and the like. Examples of the coloring agent include foodcolor, lake pigment and the like, as well as any coloring matter usable for pharmaceutical agents. Examples of the masking agent include titanium dioxide, precipitated calcium carbonate, calcium diphosphate, calcium sulfate and the like. Examples of the plasticizers include phthalic acid derivatives such as diethyl phthalate and the like, polyethylene glycol, propylene glycol, triacetine, triethyl citrate, glycerin, glycerin fatty acid ester, silicone oil and the like. Examples of the lubricant include light anhydrous silicic acid, talc, kaolin, starch and the like.

The amount of the release control film coating agent to the drug granule can be varied according to desired releaseability. In the case of a sustained release film coating agent, for example, the amount is 5% (W/W)–100% (W/W), preferably 10% (W/W)–50% (W/W), more preferably 10% (W/W)–35% (W/W), of the drug granules. In the case of an enteric film coating agent, the amount is 10% (W/W)–100% (W/W), preferably 10% (W/W)–50% (W/W), more preferably 20% (W/W)–40% (W/W), of the water soluble drug granules.

The shape of the coated granules of the present invention is subject to no particularly limitation, but from the aspect of drug releaseability, a spherical shape having the smallest surface area is preferable.

The particle size of the coated granules of the present invention is not particularly limited, but it is preferably in the range of 0.1 mm–2 mm, more preferably 0.1 mm–1.2 mm, depending on the desired releaseability and the release control film coating agent to be used. The more preferable range of particle size of the coated granules is determined according to the form of desired pharmaceutical preparation. For granule preparations or capsule preparations, for example, the particle size is preferably 0.2 mm–2 mm, more preferably 0.4 mm–1.5 mm, particularly preferably 0.6 mm–1.2 mm. For tablet preparations, for example, the particle size is preferably 0.1 mm–1 mm, more preferably 0.1 mm–0.6 mm, particularly preferably 0.2 mm–0.6 mm. The particle size of the above-mentioned coated granules can be measured in the same manner as that of the aforementioned drug nucleus.

The coated granules of the present invention may be used as granule preparation as they are, or tableted, or filled in a capsule or covered with a capsule base to give capsules.

When the drug granules or coated granules of the present invention are tableted, various additives such as disintegrant, excipient, lubricant and the like may be added. Examples of the disintegrant include carmellose, carmellose calcium, carmellose sodium, croscarmellose sodium, crospovidone, low substitution hydroxypropylcellulose, carboxymethyl starch sodium and the like. Examples of the excipient include sugars, sugar alcohols, starches, microcrystalline cellulose, calcium hydrogen phosphate, calcium dihydrogen phosphate and the like, with preference given to highly compressed excipient, such as ceolas (trademark: Asahi Chemical Industry Co., Ltd.) and cellactose (trademark: meggle GMBH). Examples of the lubricant include magnesium stearate, talc, hydrogenated oil, stearic acid, calcium stearate, gryceryl behenate, sodium stearylfumarate and the like.

The mixing ratio of the additives of the above-mentioned disintegrant, excipient, lubricant and the like is, in the case of tableting coated granules, for example, the amount of the disintegrant is not more than 30% (W/W), preferably 5% (W/W)–15% (W/W) of the coated granules. In the case of an excipient, the amount is, for example, not more than 50% (W/W), preferably 15% (W/W)–30% (W/W). In the case of a lubricant, the amount is 0.05% (W/W)–3% (W/W), preferably 0.3% (W/W)–1% (W/W). When a lubricant is added in the external lubrication system (which comprises tableting upon application of a lubricant on the tableting machine, rather than on the granules to be tableted), the amount is 0.001% (W/W)–0.2% (W/W), preferably 0.01% (W/W)–0.1% (W/W), of the coated granules.

Depending on the object, the tablets obtained from the drug granules or coated granules of the present invention may be further coated. Examples of the coating agent include those obtained by admixing a combination of a base, such as hydroxypropylmethylcellulose, hydroxypropylcellulose, methylcellulose, aminoalkyl methacrylate copolymer E, polyvinylacetal diethylaminoacetate, polyvinylpyrrolidone, pullulan and the like, and a plasticizers, such as polyethylene glycol, propylene glycol, triacetine, triethyl citrate, glycerin, glycerin fattry acid ester and the like, with additives, where necessary, such as titanium dioxide, precipitated calcium carbonate, calcium diphosphate, calcium sulfate and the like and preparing the admixture, and the like.

The pharmaceutical preparation obtained by the present invention is particularly useful for an oral administration. While the dose varies depending on the water soluble drug to be contained as an active ingredient, condition, age and sex of patients, desired duration and the like, the single dose is, for example, 50 mg–5 g, preferably 100 mg–3 g.

A production method is described in detail in the following, wherein crystal of a water soluble drug are granulated by spraying a solution of the water soluble drug to form a granule, which is coated to give a coated granule, the coated granule is tableted, and the tablets are coated.

(1) Granulation

First, a water soluble drug is dissolved in a solvent and a solution of a water soluble drug prepared as above is sprayed on the drug nucleus previously charged in a granulating apparatus to form drug granules using the drug nucleus.

The granulating apparatus to be used includes, for example, granulators classified into rotary granulation and rotary fluidized bed granulation, with preference given to rotary fluidized bed granulating coater, such as multiplex (POWREX CORPORATION).

The air supply temperature during granulation is, for example, 40° C.–100° C., preferably 70° C.–90° C.

The air exhaust temperature during granulation is, for example, 25° C.–50° C., preferably 30° C.–45° C.

The flow rate during granulation of the solution is, for example, 1 g/min–30 g/min, preferably 3 g/min–30 g/min, more preferably 3 g/min–15 g/min, most preferably 5 g/min–15 g/min, for charging 400 g, though subject to change depending on the scale of the granulator to be used, the charge amount of the drug nucleus and particle size thereof, and particle size of desired drug granules.

The air flow during granulation is 25 $m^3$/h–100 $m^3$/h, preferably 30 $m^3$/h–100 $m^3$/h, more preferably 30 $m^3$/h–70 $m^3$/h, most preferably 40 $m^3$/h–100 $m^3$/h, particularly preferably 40 $m^3$/h–70 $m^3$/h for charging 400 g, though subject to change depending on the scale of the granulator to be used, the charge amount of the drug nucleus, particle size thereof, and particle size of desired drug granules.

The rotation rate of the rotor plate during granulation varies depending on the scale of the granulator to be used and the charge amount of the drug nucleus. For charging 400 g, for example, it is 50 rpm–500 rpm, preferably 100 rpm–350 rpm.

The position of the spray nozzle during granulation varies depending on the granulator to be used, and particle size of the drug nucleus. In the case of rotary fluidized bed granulate coater, top spray and tangential spray are selected. When the particle size of at least drug nucleus, from among the drug nucleus and drug granule, is not more than 100 µm, top spray is preferable. When the particle size of at least drug nucleus, from among the drug nucleus and drug granule, is not less than 300 µm, tangential spray is preferable.

The spray air flow during granulation varies depending on the scale of the granulator to be used, flow rate and the position of the spray nozzle. In the case of charging 400 g and tangential spray, for example, the spray air flow is 15 L/min–50 L/min, preferably 20 L/min–40 L/min. The side air flow is 20 L/min–100 L/min, preferably 35 L/min–60 L/min.

The diameter of the spray nozzle during granulation varies depending on the scale of the granulator to be used and flow rate. In the case of charging 400 g at a flow rate of 10 g/min, for example, the diameter is 0.5 mm–2.0 mm.

(2) Drying

The drug granules obtained in the above-mentioned (1) are dried. The drug granules are dried under depressurization or atmospheric pressure until the amount of reduction by drying as measured by an infrared moisture meter becomes, for example, within 3% (W/W), preferably within 2% (W/W). The drying is conducted in the above-mentioned granulator.

(3) Coating of Drug Granule

A solution or a dispersion of a release control film coating agent is sprayed on the drug granules containing the water soluble drug obtained in the above-mentioned (1) and (2) for coating.

The coating apparatus to be used includes, for example, coating apparatuses classified into fluidized bed coating, rotary coating and rotary fluidized bed coating, with preference given to rotary fluidized bed granulating coater, bottom spray type fluidized bed coater and the like.

The air supply temperature during coating varies depending on the coating agent. When, for example, AQUA Coat is used, it is 50° C.–100° C., preferably 60° C.–80° C. When, for example, Eudragit RS30D, Eudragit RL30D or a mixture thereof is used, it is 50° C.–100° C., preferably 50° C.–75°

C. When Eudragit NE30D is used, it is 30° C.–80° C., preferably 40° C.–60° C.

The air exhaust temperature during coating varies depending on the coating agent. When, for example, AQUA Coat is used, it is 30° C.–50° C., preferably 35° C.–45° C. When, for example, Eudragit RS30D, Eudragit RL30D or a mixture thereof is used, it is 30° C.–45° C., preferably 30° C.–40° C. When Eudragit NE30D is used, it is 20° C.–40° C., preferably 25° C.–35° C.

The flow rate granulate during coating varies depending on the scale of the coating apparatus to be used and the charge amount of the drug granules. Amount of the solution of the release control coating agent is, for example, 3 g/min–30 g/min, preferably 5 g/min–15 g/min, for charging 400 g.

The air flow during coating is 30 m$^3$/h–100 m$^3$/h, preferably 40 m$^3$/h–70 m$^3$/h, for charging 400 g, though subject to change depending on the scale of the coating apparatus to be used and the charge amount of the drug granules.

The rotation rate of the rotor plate during coating varies depending on the scale of the coating apparatus to be used and the charge amount of the drug granules. For charging 400 g, for example, it is 50 rpm–500 rpm, preferably 100 rpm–250 rpm.

The position of the spray nozzle during coating varies depending on the coating apparatus to be used. In the case of rotary fluidized bed granulate coater, top spray and tangential spray, preferably tangential spray, are selected. In the case of fluidized bed granulate coating machine, top spray and bottom spray, preferably bottom spray, are selected.

The spray air flow during coating varies depending on the scale of the coating appratus to be used and the position of the spray nozzle. In the case of charging 400 g and tangential spray, for example, the spray air flow is 15 L/min–50 L/min, preferably 20 L/min–40 L/min. The side air flow is 20 L/min–100 L/min, preferably 35 L/min–60 L/min.

The diameter of the spray nozzle during coating varies depending on the scale of the coating apparatus to be used and flow rate. In the case of charging 400 g and flow rate of 10 g/min, for example, the spray air flow is 0.5 mm–2.0 mm, preferably 0.8–1.2 mm.

(4) Drying of Coated Granules

The drug granules obtained the above-mentioned (3) are dried under depressurization or atmospheric pressure until the amount of reduction by drying as measured by an infrared moisture meter becomes, for example, within 3% (W/W), preferably within 2% (W/W). As a drier, for example, a drying oven (Constant Temperature Oven Dk83, Yamato Scientific Co., LTD.) is exemplified.

(5) Admixing

For tableting, the coated granules obtained in (4) are admixed with disintegrant, excipient, lubricant and the like.

As a mixing apparatus, a mixer classified under Diffusion mixers (Tumble) is used. Preferably, Tumble blender, V blender, Double cone or Bin tumbler are used as a mixer.

(6) Tableting

The mixture of (5) is tableted with a punch to give tablets. The tableting pressure is, for example, 5 kg–30 kg.

For tableting, tableting machines classified under Tablet Press are used.

(7) Coating of Tablet

The tablet obtained in (6) is coated as necessary depending on the object.

As a coating apparatus, for example, apparatuses classified under coating pan are used, which are preferably apparatuses classified under Perforated Coating System.

(8) Drying of Coating Tablet

The drying is conducted under depressurization or atmospheric pressure until the amount of reduction by drying as measured by an infrared moisture meter becomes, for example, within 3% (W/W), preferably within 2% (W/W). The drying is conducted in the above-mentioned coating apparatuses.

EXAMPLES

The present invention is explained in the following by referring to Examples, which are intended only for explaining the present invention without limitation in any way.

Examples 1–3

Using a rotary fluidized bed granulate coating apparatus (multiplex MP-01, POWREX CORPORATION), aqueous solution (30% W/W of metformin hydrochloride (N,N-dimethylimidodicarbonimidicdiamide hydrochloride), dissolved at 25° C.) was gradually sprayed on single crystals (prismatic crystals) of metformin hydrochloride charged in the apparatus in advance. This step was repeated and the granules were dried (amount of reduction by drying as measured by an infrared moisture meter: 2% W/W). After drying, the granules were classified to give 1200 g of spherical drug granules having a particle size of 500 μm–840 μm consisting of metformin hydrochloride alone.

Figure 2:
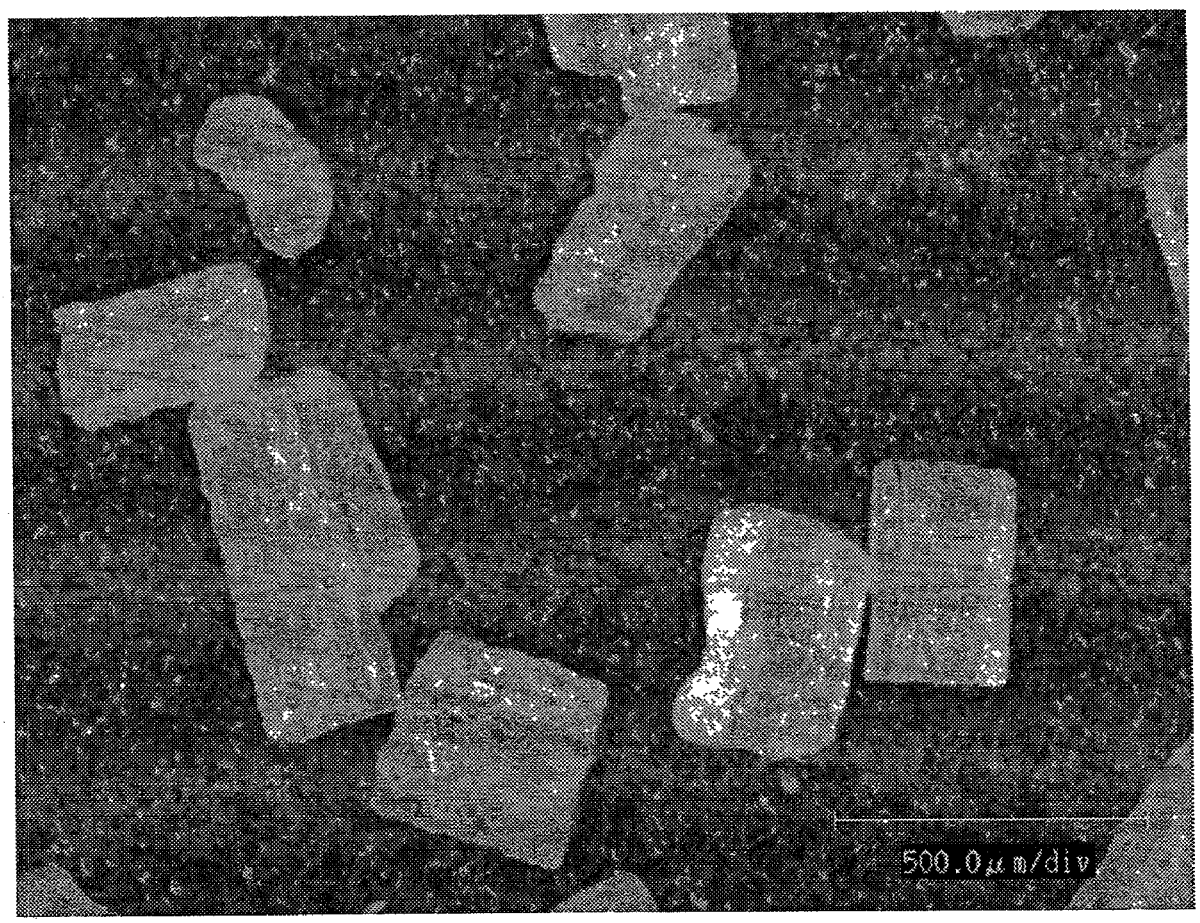
FIG. 2 is a photograph showing drug granules after the first granulation in Examples 1–3.
Figure 3:
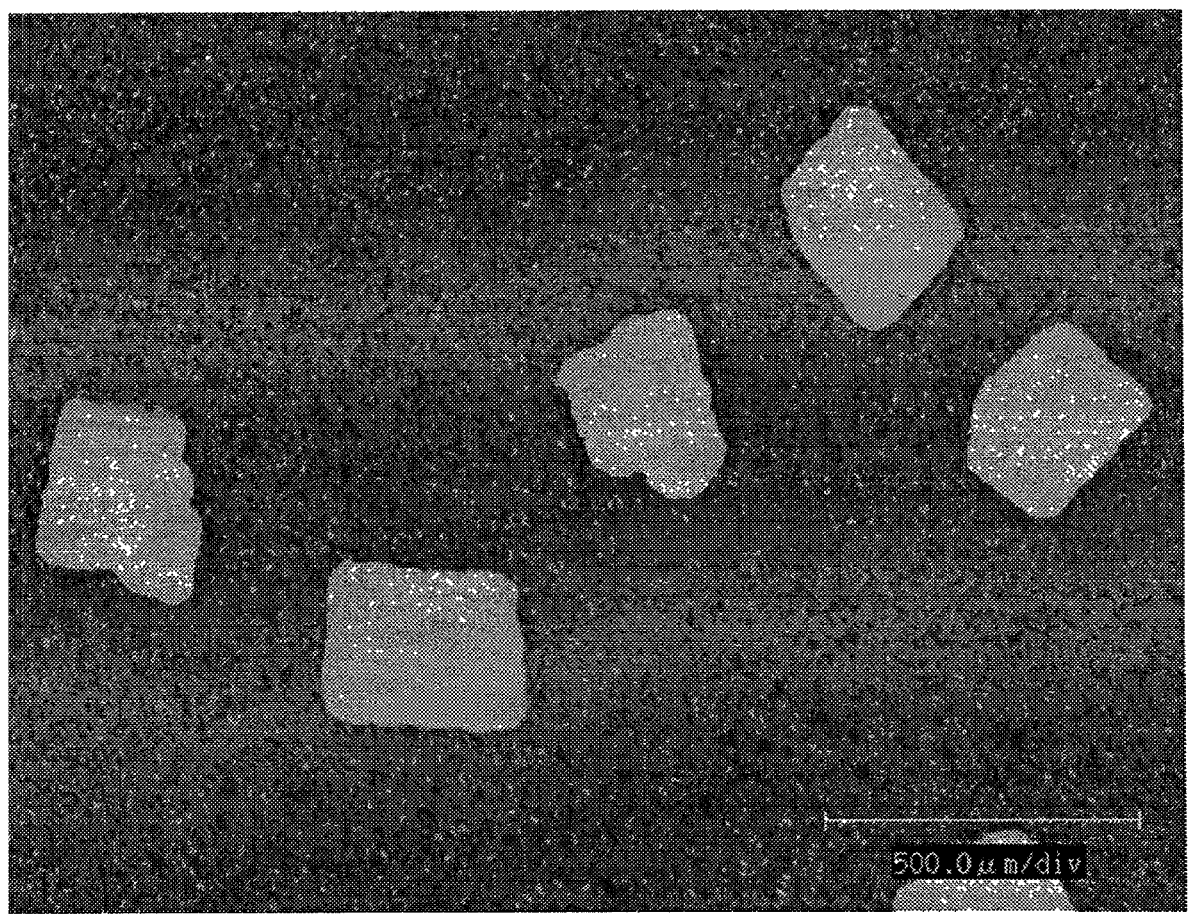
FIG. 3 is a photograph showing drug granules after the third granulation in Examples 1–3.
Figure 4:
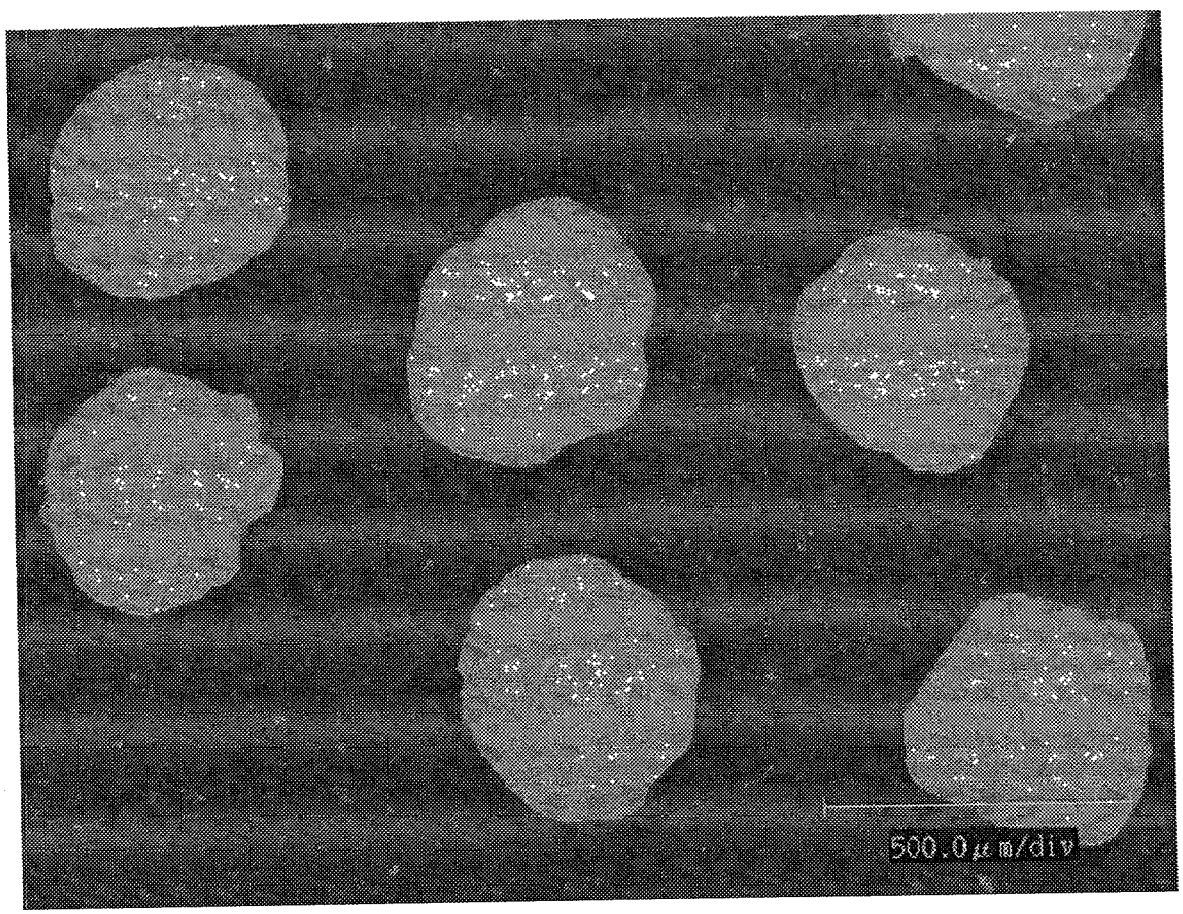
FIG. 4 is a photograph showing drug granules after the fifth granulation in Examples 1–3.
Figure 5:
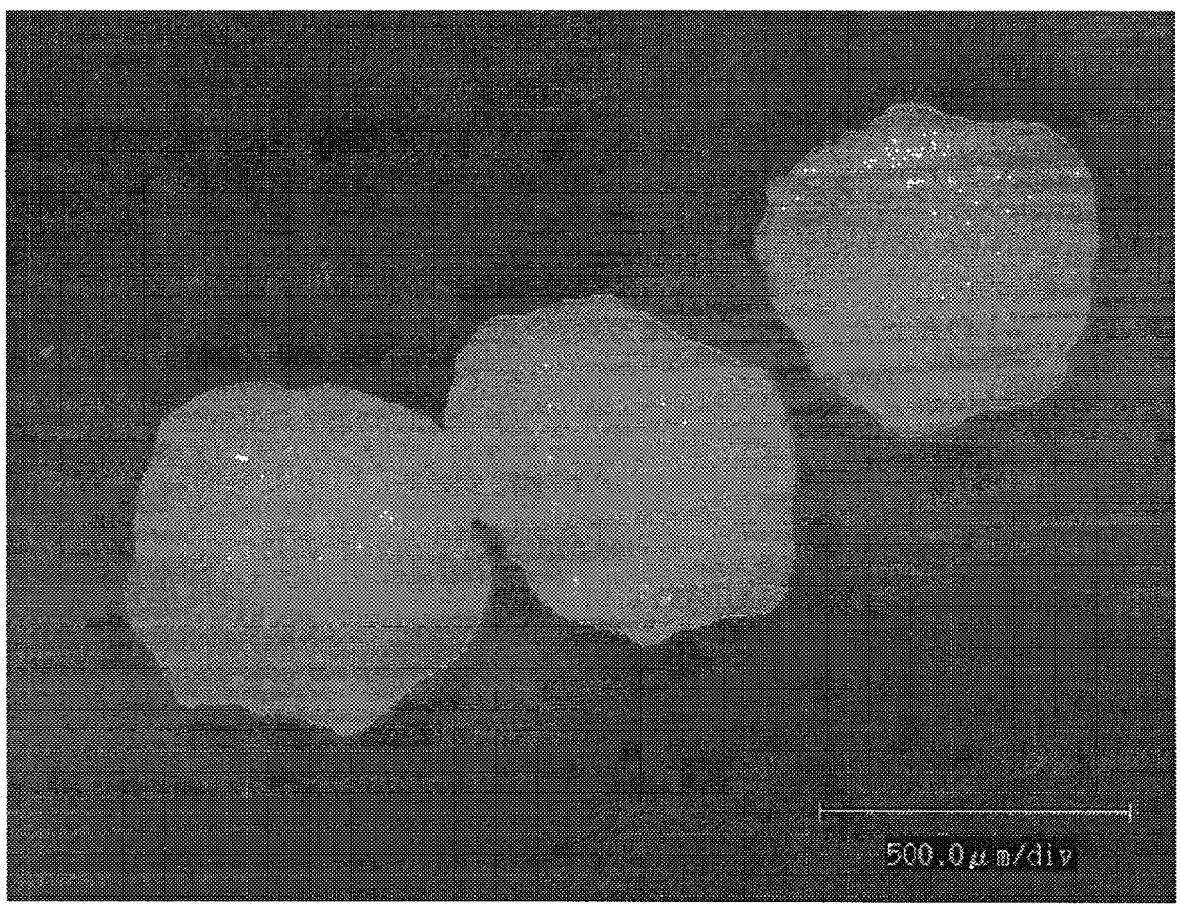
FIG. 5 is a photograph showing drug granules after the seventh granulation in Examples 1–3.
Figure 6:
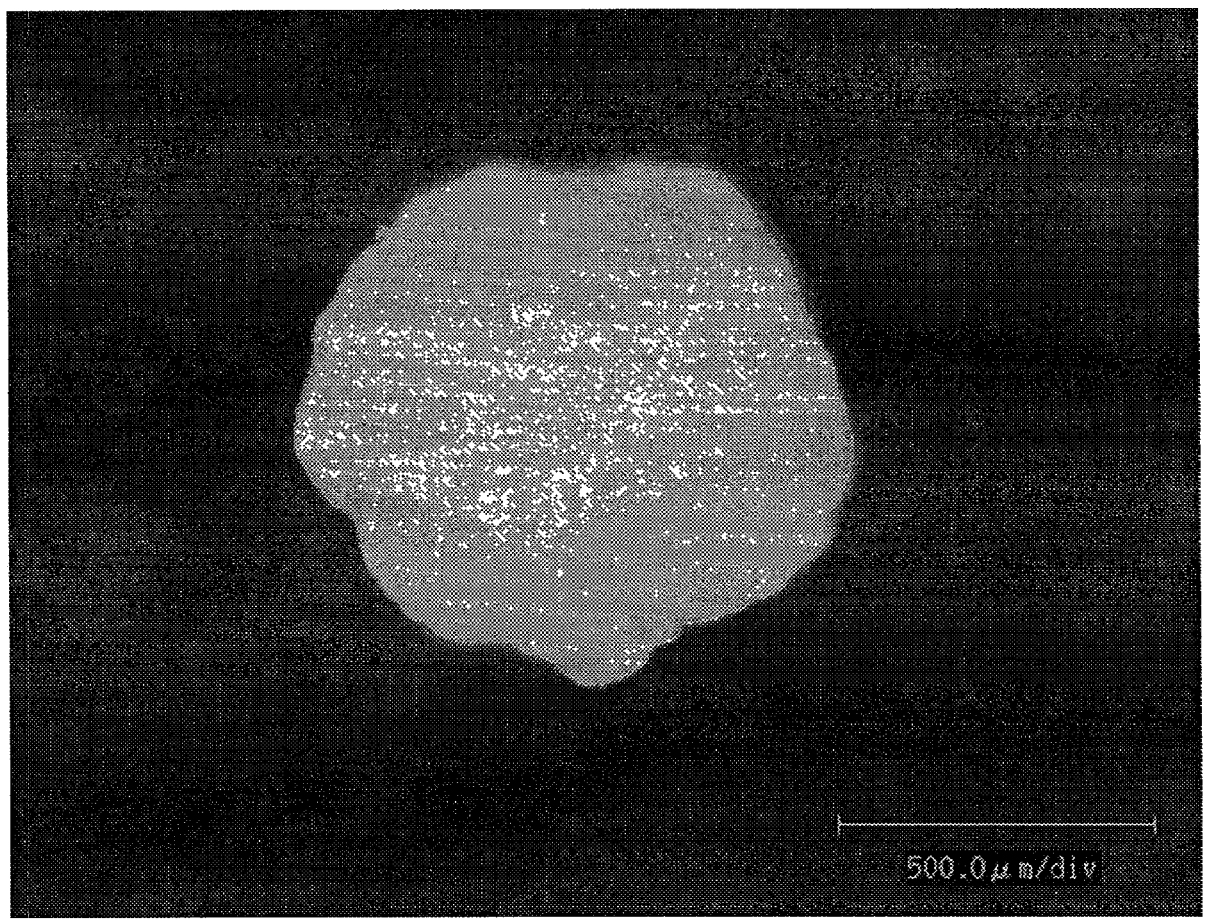
FIG. 6 is a photograph showing drug granules after the ninth granulation in Examples 1–3.

In granulating, an aqueous solution of a water soluble drug was sprayed on prismatic single crystals as shown in FIG. 1 of the water soluble drug to give sphere-like drug granules shown in FIG. 2 (granulation once), FIG. 3 (granulation 3 times), FIG. 4 (granulation 5 times) and FIG. 5 (granulation 7 times), and spherical drug granules shown in FIG. 6 (granulation 9 times).

In Table 1, the charge amounts of metformin hydrochloride single crystals or metformin hydrochloride granules, formulation conditions of the spray solution (aqueous metformin hydrochloride solution) and obtained amount of each step are shown.

TABLE 1

| granulation (times) | | 1 | 2 | 3 | 4 | 5 | 6 | 7 | 8 | 9 |
|---|---|---|---|---|---|---|---|---|---|---|
| charge amount | | 500 | 500 | 490 | 455 | 722 | 500 | 500 | 400 | 800 |
| spray solution | metformin hydrochloride | 300 | 500 | 500 | 500 | 720 | 500 | 500 | 600 | 900 |
| | purified water | 1000 | 1667 | 1667 | 1667 | 2400 | 1667 | 1667 | 2000 | 3000 |
| obtained amount | | 704 | 989 | 910 | 881 | 1419 | 928 | 801 | 835 | 1427 |

Unit: g

The production conditions were as follows.

<1 to 6 Times>
spray nozzle type: top spray, spray nozzle position: lower, air supply temperature: 65° C.–85° C., air exhaust temperature: 34° C.–43° C., air flow: 50 m³/h, rotation rate of rotor plate: 250 rpm–350 rpm, spray air pressure: 1.2 kgf/cm²–1.4 kgf/cm², spray air flow: 25 L/min, spray rate (flow rate): 6 g/min–15 g/min <7 to 9 Times>
spray nozzle type: side spray, spray nozzle position: lower, air supply temperature: 75° C.–90° C., air exhaust temperature: 34° C.–39° C., air flow: 50 m³/h, rotation rate of rotor plate: 250 rpm, spray air pressure: 2.8 kgf/cm², spray air flow: 25 L/min, side air flow: 45 L/min, spray rate (flow rate): 10 g/min–15 g/min The spherical drug granules (1200 g) obtained above was divided by 400 g and each coated with an aqueous solution of a release control film coating agent having a composition shown in the following Table 2 in a rotary fluidized bed granulate coating apparatus (as mentioned above), after which the granules were dried in a drying apparatus (as mentioned above) to respectively give sustained release coated granules of metformin hydrochloride (particle size of Example 1: 710 μm–1000 μm, particle size of Example 2: 710 μm–1000 μm, particle size of Example 3: 710 μm–1000 μm). The amount of reduction by drying as measured by an infrared moisture meter was 0.2% (W/W) for Example 1, 0.3% (W/W) for Example 2 and 0.3% (W/W) for Example 3.

TABLE 2

| Composition | Example 1 | Example 2 | Example 3 |
|---|---|---|---|
| AQUA Coat (Asahi Chemical Industry Co., LTD.) (solid content) | 667 (200) | — | — |
| Eudragit RS30D (ROHM CO., LTD.) (solid content) | — | 667 (200) | — |
| Eudragit NE30D (ROHM CO., LTD.) (solid content) | — | — | 667 (200) |
| triethyl citrate | 60 | 20 | — |
| glyceryl monostearate | — | 10 | 10 |
| water | 273 | 303 | 323 |
| total | 1000 | 1000 | 1000 |

Unit: g

The production conditions were as follows.

<Production Conditions>
In this step, 10% of the spray solution was used for first coat and then second coat was applied. The common conditions for three film coating agents are shown in Table 3, different aspects of the three film coating agents are shown in Table 4.

TABLE 3

| conditions | nozzle type | nozzle position | rotor | air pressure | spray air flow | side air flow | spray rate |
|---|---|---|---|---|---|---|---|
| First coat | top | lower | 100 rpm | 1.4 kgf/cm² | 25 L/min | — | 3.3 g/min |
| Second coat | side | lower | 200 rpm | 1.4 kgf/cm² | 25 L/min | 45 L/min | 10 g/min |

TABLE 4

| conditions | Example 1 | | Example 2 | | Example 3 | |
|---|---|---|---|---|---|---|
| | First coat | Second coat | First coat | Second coat | First coat | Second coat |
| air supply temp. (° C.) | 70 | 65–80 | 55 | 67–70 | 55 | 45–47 |
| air exhaust temp. (° C.) | 42 | 35–40 | 35 | 33–35 | 35 | 24–27 |
| drying condition | 60° C. × 8 h | | 50° C. × 12 h | | 40° C. × 60 h (tight sealed) | |

Evaluation Test 1

Figure 7:
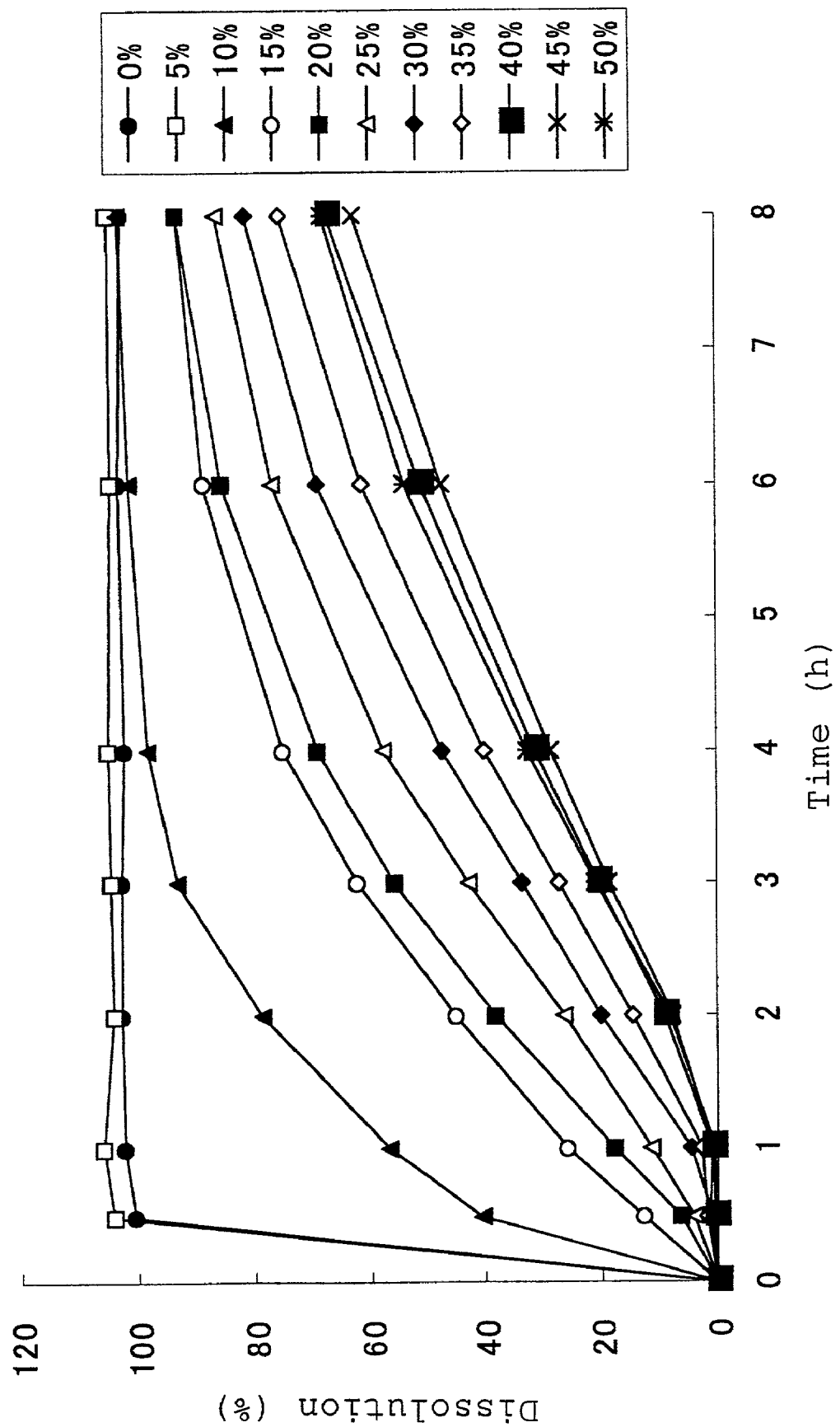
FIG. 7 is a graph showing the evaluation test results of dissolution of metformin hydrochloride from the coated granules obtained by coating spherical drug granules made of metformin hydrochloride alone with a release control film coating agent, wherein the horizontal axis is time (h) and the ordinate axis is dissolution rate (%) of metformin hydrochloride.

In the same manner as in Example 1 above, spherical drug granules consisting only of metformin hydrochloride were coated with increasing amounts of AQUA Coat as a coating agent to give samples of the coated granules, and dissolution of main drug from the preparations was evaluated according to Japan Pharmacopoeia, dissolution test method 2 (Paddle method). The results are shown in FIG. 7. In FIG. 7, the values of the legends show the calculated weight ratio of solid content of AQUA Coat to the spherical drug granule consisting only of metformin hydrochloride. As shown in FIG. 7, the dissolution of metformin hydrochloride was delayed along with increase in the amount of coating of the AQUA Coat.

The above-mentioned evaluation test was conducted under the following analysis conditions.

<Analysis Conditions>
test solution: purified water
amount of solution: 900 mL
temperature of solution: 37° C.
number of rotation: 100 rpm
sampling time: 0.5, 1, 2, 3, 4, 6, 8 hours later
sampling amount: 5 mL
measurement method: sample solution was diluted 50-fold with water and absorption at 222 nm was measured.

Examples 4–6

Magnesium stearate (0.1 g, Taihei Chem. Co.) was added to the coated granules (10 g, weight ratio of solid content as coating to spherical drug granules: 50%) obtained in each of the above-mentioned Examples 1–3 and mixed thoroughly. The each obtained mixture (750 mg) was compressed using a tableting apparatus (tableting tester SK-02, SANKYO PIO-TECH CO., LTD., inner diamiter of mortar: 11 mm) at tableting pressure of 1.5 t to give tablets of Examples 4–6 corresponding to each of the above-mentioned coated granules of Examples 1–3.

The properties of the tablets of Examples 4–6 are respectively shown in Table 5. The tableting pressure in Table 5 was measured using a tablet breaking strength measurement apparatus (Toyama Sangyo Co., LTD.).

TABLE 5

| | Example 4 (AQUA Coat coating) | Example 5 (Eudragit RS30D coating) | Example 6 (Eudragit NE30D coating) |
|---|---|---|---|
| Thickness (mm) | 6.3 | 6.4 | 7.4 |
| tableting pressure (kg) | 6.6 | 0.7 | 2.0 |

Evaluation Test 2

Figure 8:
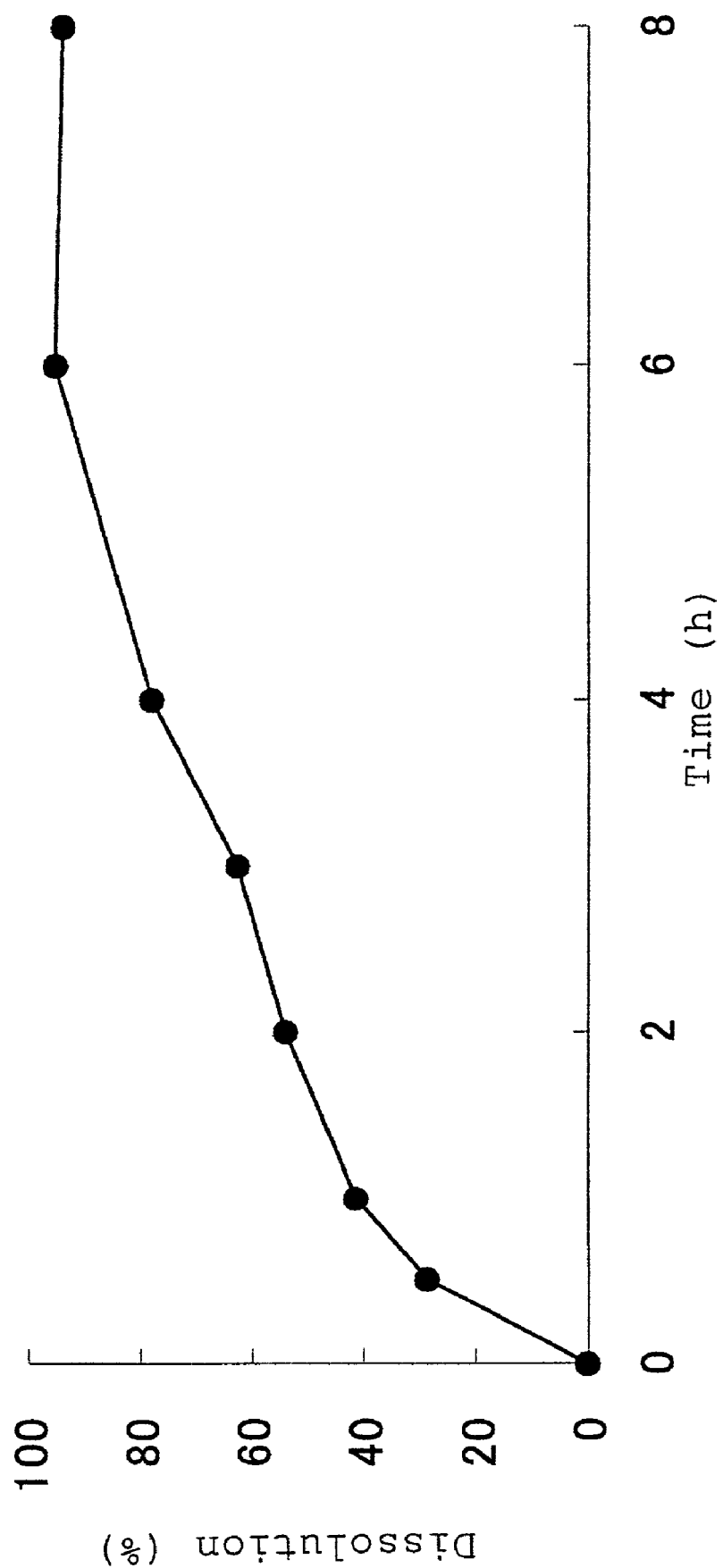
FIG. 8 is a graph showing the evaluation test results of dissolution of metformin hydrochloride from the tablet preparation of Example 4, wherein the horizontal axis is time (h) and the ordinate axis is dissolution rate (%) of metformin hydrochloride.
Figure 9:
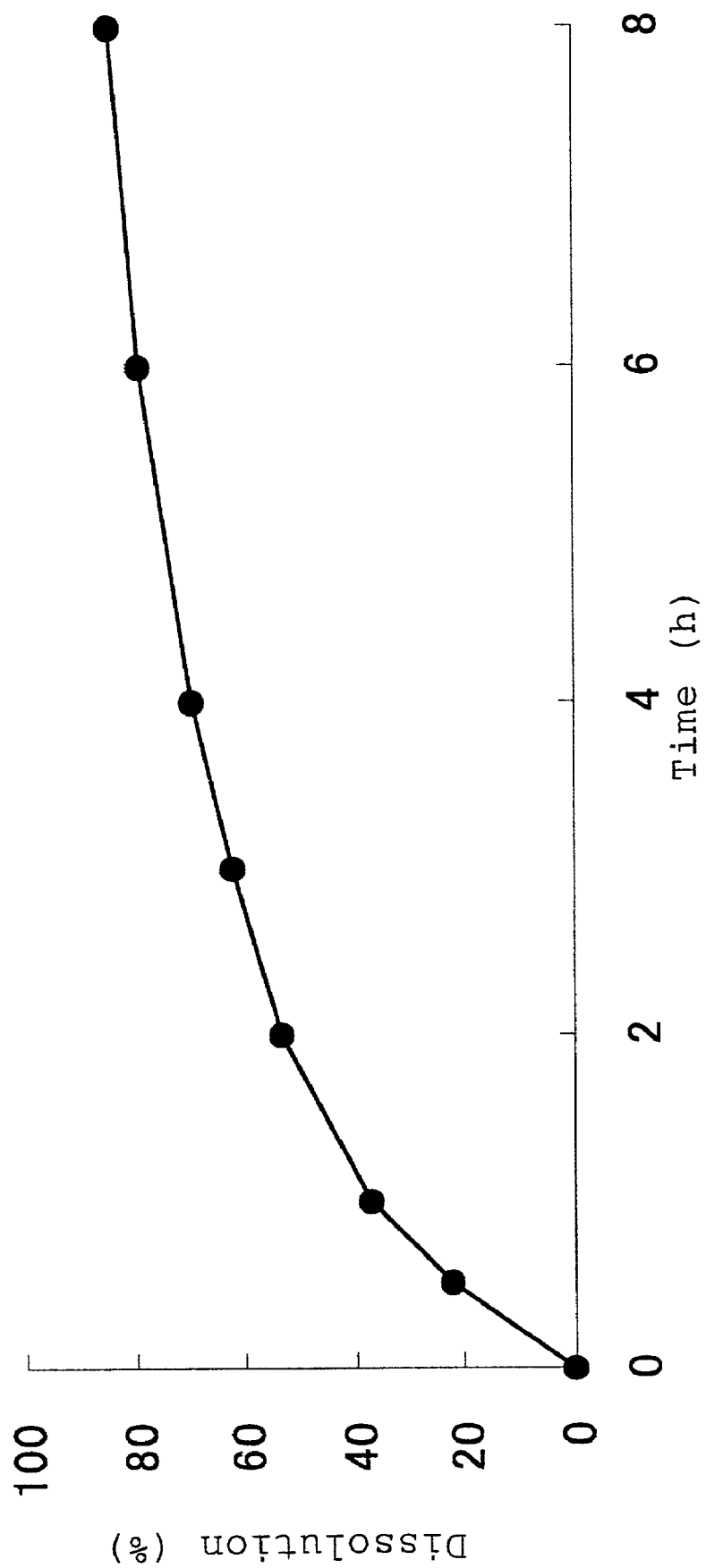
FIG. 9 is a graph showing the evaluation test results of dissolution of metformin hydrochloride from the tablet preparation of Example 5, wherein the horizontal axis is time (h) and the ordinate axis is dissolution rate (%) of metformin hydrochloride.
Figure 10:
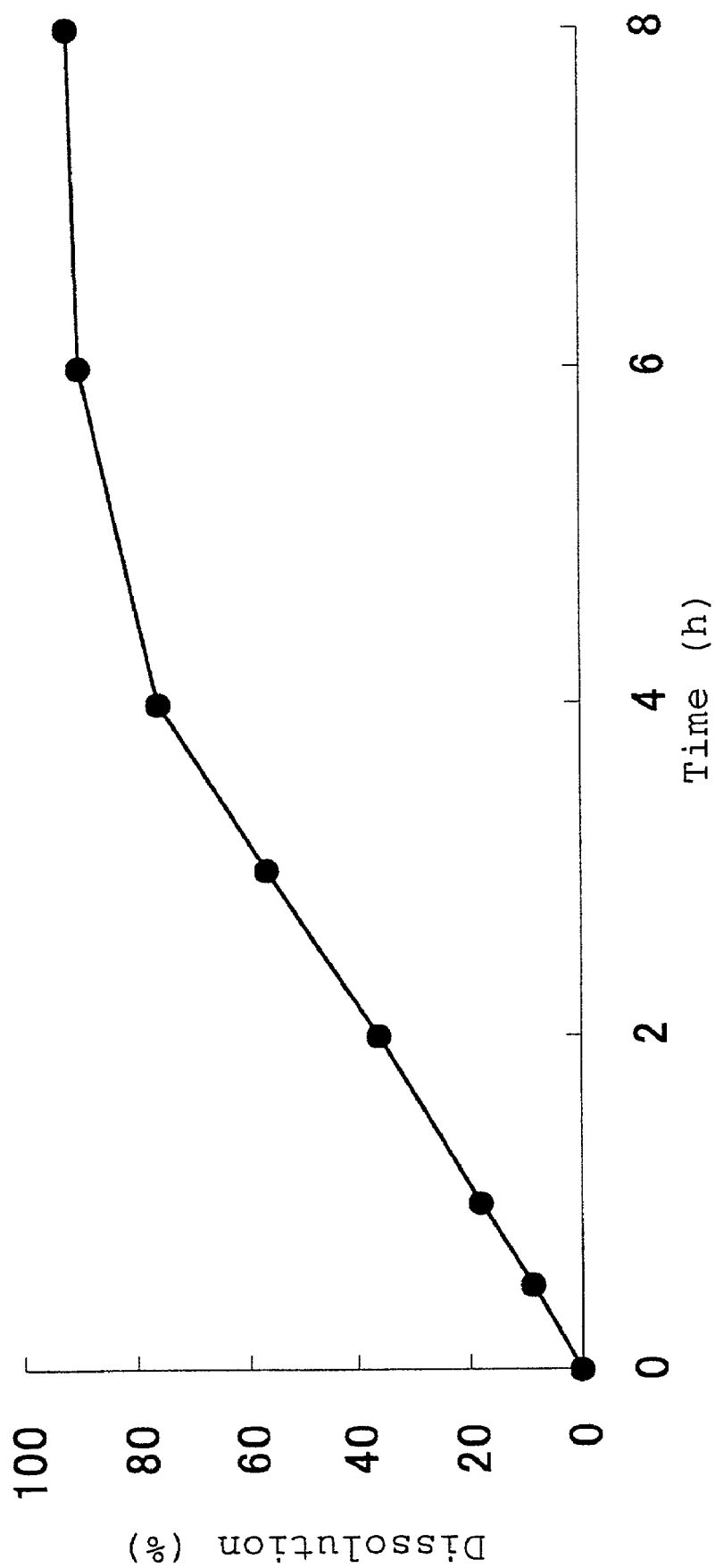
FIG. 10 is a graph showing the evaluation test results of dissolution of metformin hydrochloride from the tablet preparation of Example 6, wherein the horizontal axis is time (h) and the ordinate axis is dissolution rate (%) of metformin hydrochloride.

The dissolution of main drug from the preparations was evaluated for each tablet obtained in the above-mentioned Examples 4–6 according to Japan Pharmacopoeia, dissolution test method 2 (Paddle method). FIG. 8 is a graph showing the evaluation test results of the dissolution of main drug from lo the tablet (AQUA Coat coating) of Example 4; FIG. 9 is a graph showing the evaluation test results of the dissolution of main drug from the tablet (Eudragit RS30D coating) of Example 5; FIG. 10 is a graph showing the evaluation test results of the dissolution of main drug from the tablet (Eudragit NE30D coating) of Example 6. As shown in FIGS. 8–10, the tablets obtained by punching out the coated granules of the present invention respectively showed delayed dissolution of metformin hydrochloride.

The analysis conditions of the evaluation test were the same as in the aforementioned evaluation test 1.

Example 7

Using a rotary fluidized bed granulate coating apparatus (Multiplex MP-01, POWREX CORPORATION), an aqueous solution (23%, w/w, dissolved at 25° C.) of ethydronate disodium ((1-hydroxyethylidene) bis-phosphonate disodium) was gradually sprayed on the single crystals of ethydronate disodium charged in the apparatus in advance. The granules were classified to give 615 g of spherical drug granules consisting only of ethydronate disodium (250–500 μm).

Figure 11:
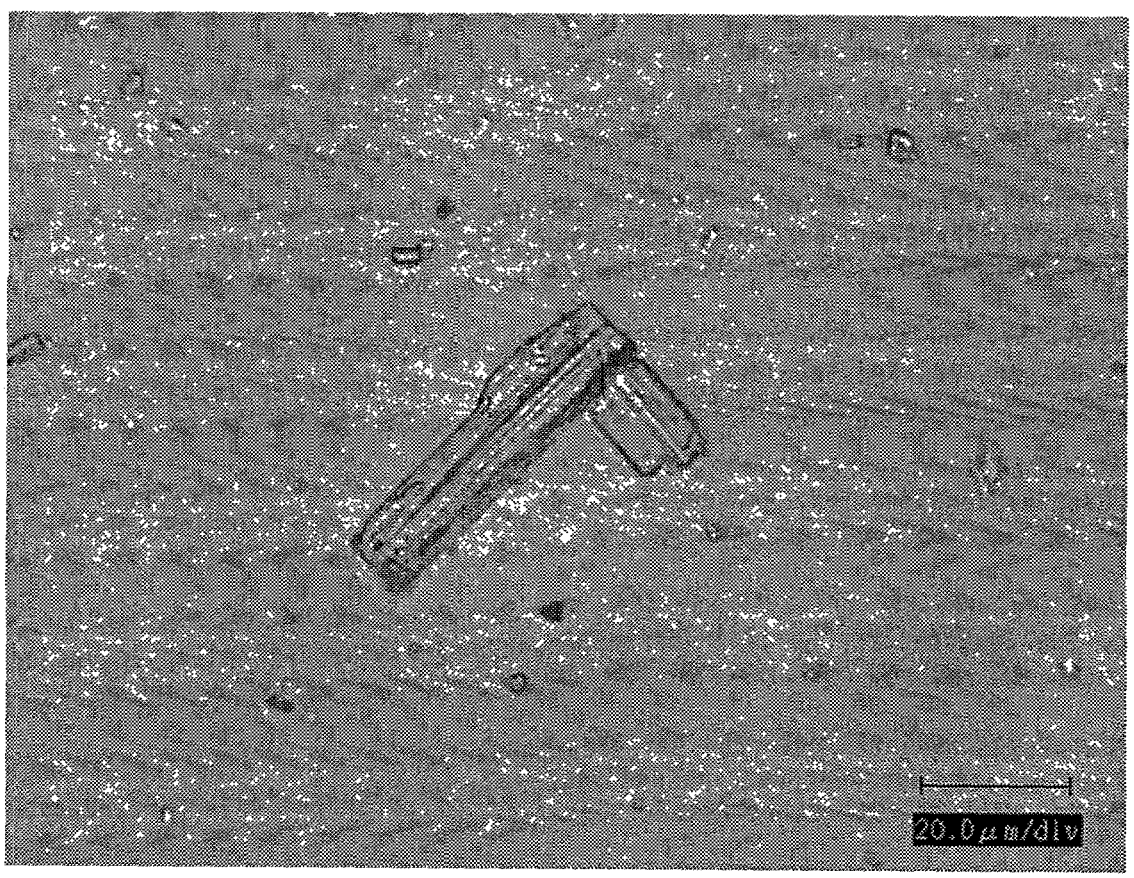
FIG. 11 is a photograph showing the single crystal of etidronate disodium used as drug nucleus in Example 7.
Figure 12:
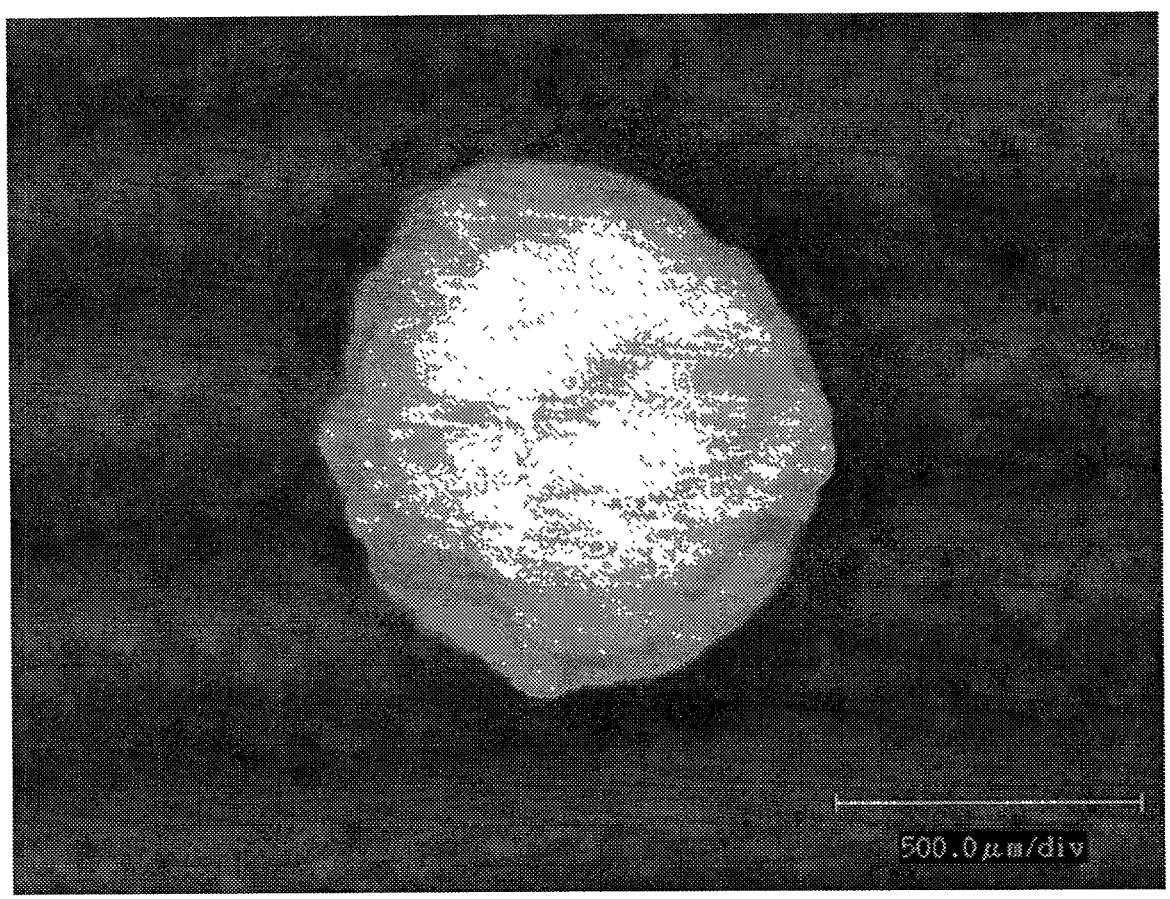
FIG. 12 is a photograph showing drug granules obtained in Example 7.

In granulating, an aqueous solution of a water soluble drug (ethydronate disodium) was sprayed on the needle-like single crystals of the water soluble drug as shown in FIG. 11 to grow spherical particles to ultimately give spherical drug granules shown in FIG. 12.

The production conditions were as follows.
spray nozzle type: top spray, spray nozzle position: lower, air supply temperature: 70° C.–84° C., air exhaust temperature: 35° C.–45° C., air flow: 40 m$^3$/h–50 m$^3$/h, rotation rate of rotor plate: 100 rpm–350 rpm, spray air pressure: 1.2 kgf/cm$^2$–1.4 kgf/cm$^2$, spray air flow: 25 L/min, spray rate (flow rate): 8 g/min–13 g/min

Example 8

Using a rotary fluidized bed granulate coating apparatus (Multiplex MP-01, POWREX CORPORATION), an aqueous cimetidine solution (30%, w/w, dissolved at 25° C.) having a pH adjusted with hydrochloric acid was gradually sprayed on the single crystals of cimetidine charged in the apparatus in advance. The granules were classified to give 438 g of drug granules on the way to spheres of cimetidine (250–500 μm) without a binder.

Figure 13:
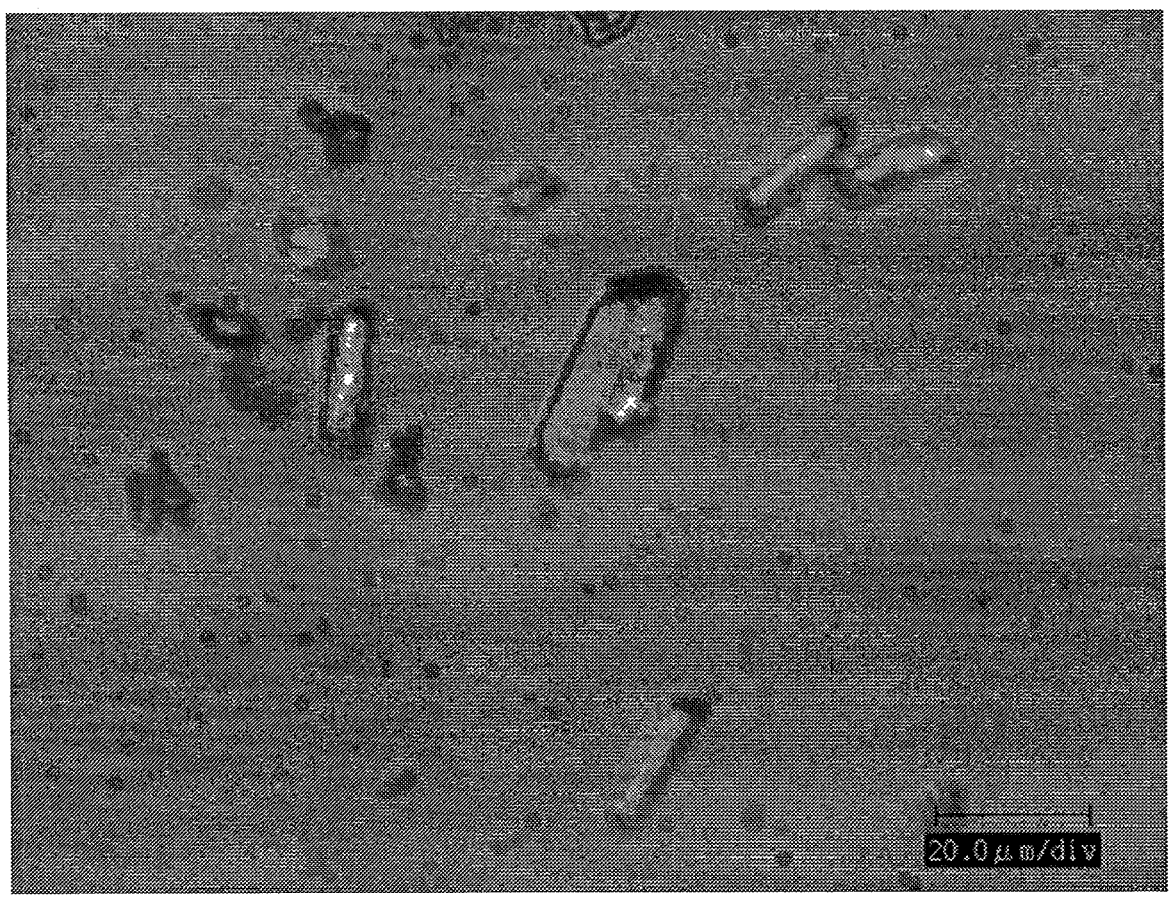
FIG. 13 is a photograph showing single crystal of cimetidine used as a drug nucleus in Example 8.
Figure 14:
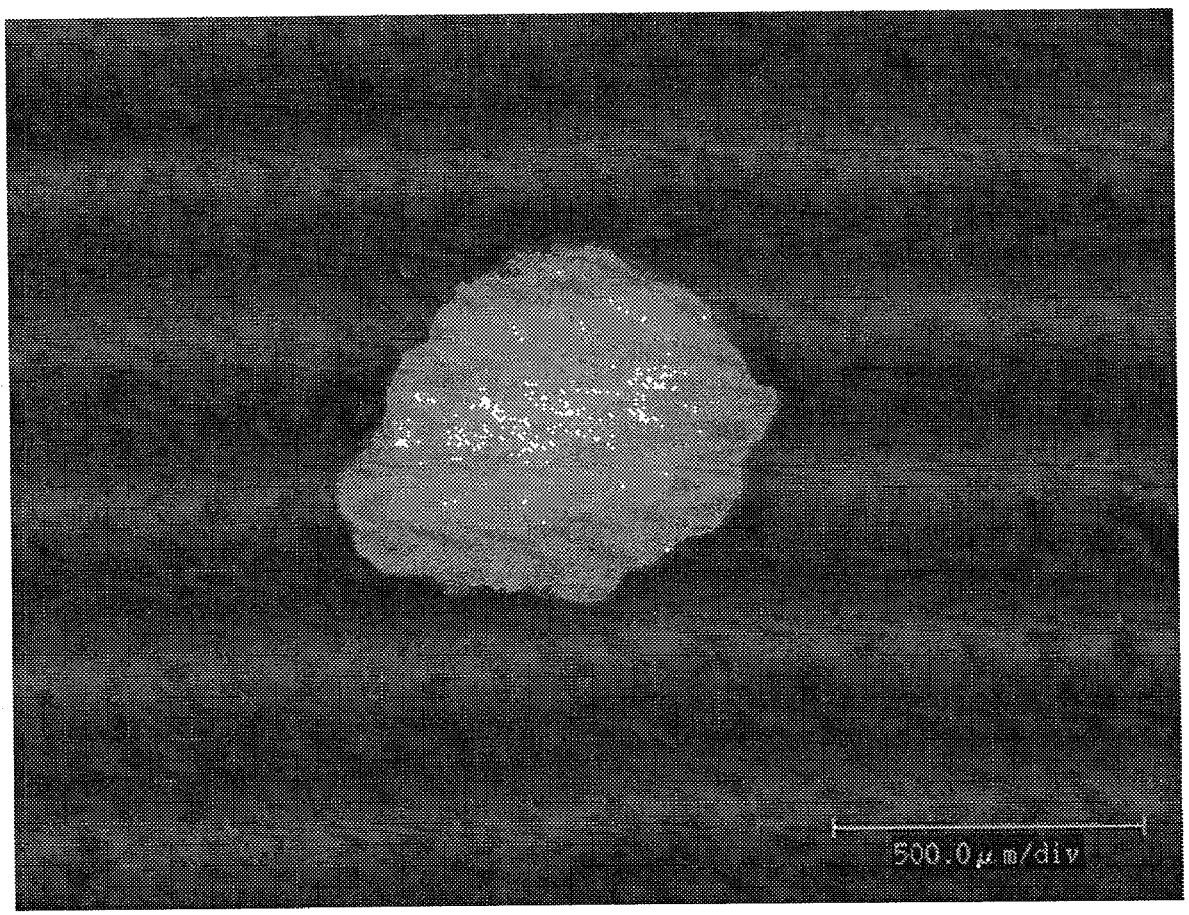
FIG. 14 is a photograph showing the drug granules obtained in Example 8.

In glanulation, an aqueous solution of a water soluble drug (cimetidine) was sprayed on the needle-like single crystals of the water soluble drug as shown in FIG. 13 to grow spherical particles to give spherical drug granules shown in FIG. 14 on the way to spheres.

The production conditions were as follows.
spray nozzle type: top spray, spray nozzle position: lower, air supply temperature: 75° C.–80° C., air exhaust temperature: 39° C.–40° C., air flow: 30–60 m$^3$/h, rotation rate of rotor plate: 100 rpm–200 rpm, spray air pressure: 1.0 kgf/cm$^2$–1.8 kgf/cm$^2$, spray air flow: 30 L/min, spray rate (flow rate): 3 g/min

Example 9

Using a rotary fluidized bed granulate coating apparatus (Multiplex MP-01, POWREX CORPORATION), an aqueous carbocisteine solution (19%–31%, w/w. dissolved at 25° C.) having a pH adjusted with sodium hydroxide was gradually sprayed on the single crystals of carbocisteine charged in the apparatus in advance. This step was repeated and the crystals were dried (amount of reduction by drying as measured by an infrared moisture meter: 0.1% W/W). After drying, the granules were classified to give 1045 g of spherical drug granules of carbocisteine (420–850 μm) without a binder.

Figure 15:
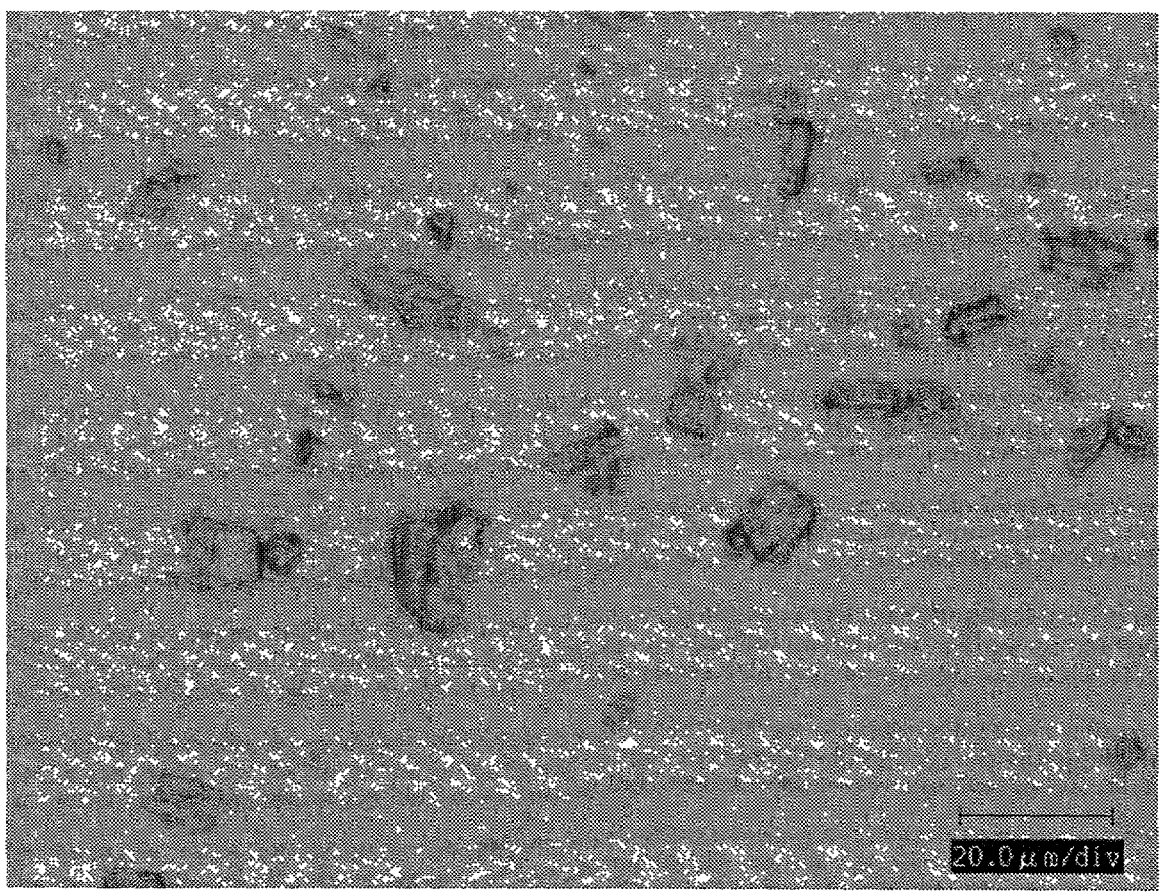
FIG. 15 is a photograph showing single crystal of carbocisteine used as a drug nucleus in Example 9.
Figure 16:
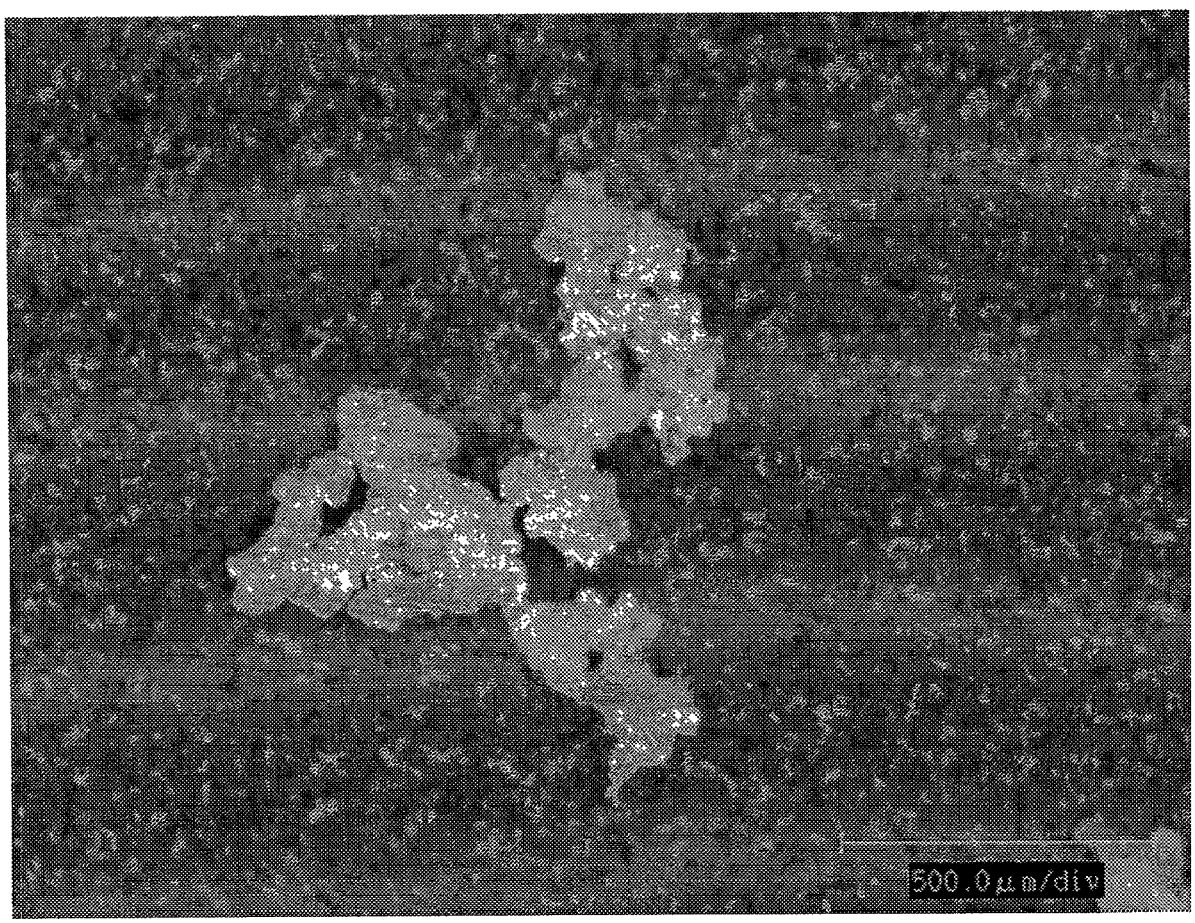
FIG. 16 is a photograph showing the drug granules after granulating once as obtained in Example 9.
Figure 17:
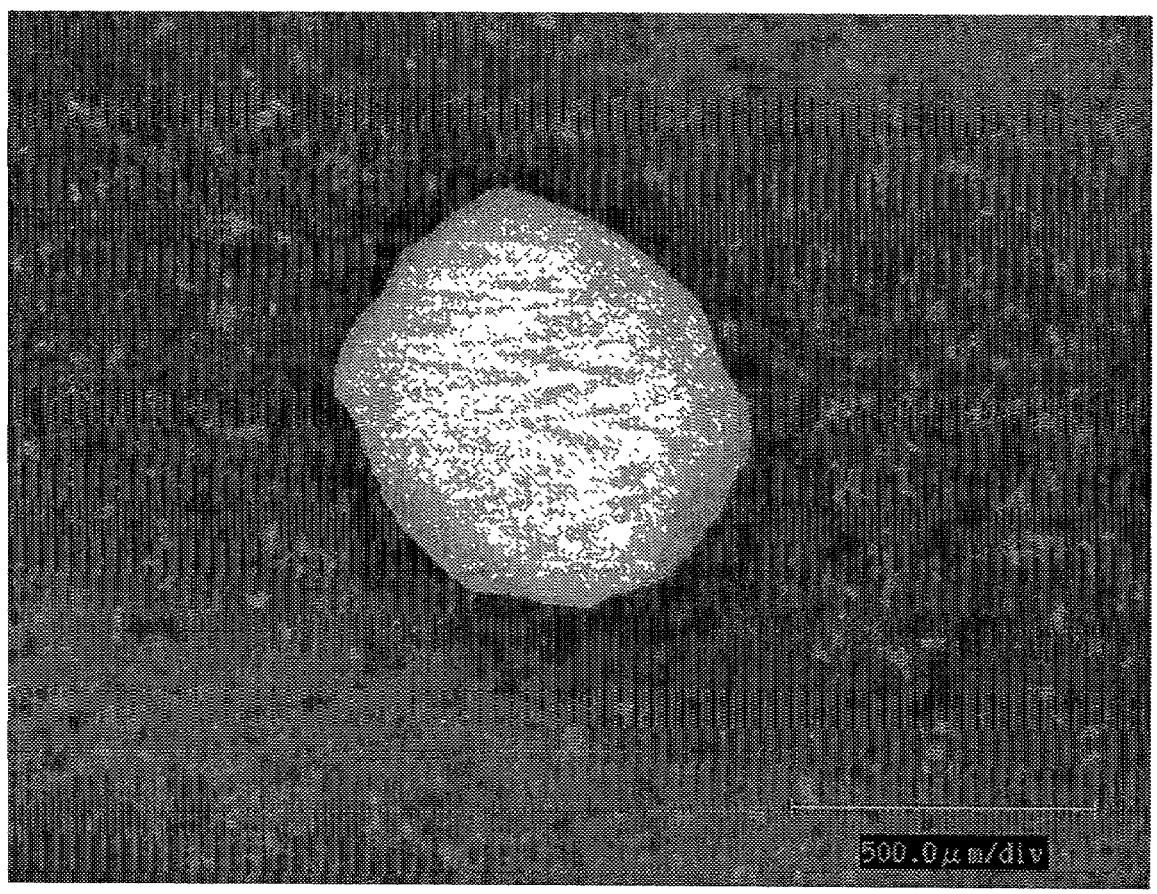
FIG. 17 is a photograph showing the drug granules after granulating 4 times as obtained in Example 9.

In granulating, an aqueous solution of the water soluble drug (carbocisteine) was sprayed on the single granules of the water soluble drug as shown in FIG. 15 to gradually grow spherical particles to give the drug granules shown in FIG. 16 by granulation once and spherical drug granules shown in FIG. 17 by granulation 4 times.

In Table 6, the charge amounts of carbocisteine single crystals or carbocisteine granules, formulation conditions of the spray solution (aqueous carbocisteine solution) and obtained amount of each step are shown.

TABLE 6

| spraying (times) | | 1 | 2 | 3 | 4 | 5 | 6 |
|---|---|---|---|---|---|---|---|
| charge amount | | 500 | 500 | 500 | 500 | 500 | 500 |
| spray solution | drug | 250 | 250 | 250 | 250 | 500 | 500 |
| | purified water | 500 | 1000 | 1000 | 1000 | 2000 | 2000 |
| | pH adjusting agent | 67 | 67 | 67 | 67 | 134 | 134 |
| Obtained amount | | 760 | 638 | 752 | 754 | 1029 | 1051 |

Unit: g

The production conditions were as follows.

<First Time>
spray nozzle type: top spray, spray nozzle position: lower, air supply temperature: 75° C.–80° C., air exhaust temperature: 36° C.–42° C., air flow: 30–50 m$^3$/h, rotation rate of rotor plate: 100 rpm–150 rpm, spray air pressure: 0.8 kgf/cm$^2$–1.2 kgf/cm$^2$, spray air flow: 25 L/min, spray rate (flow rate): 4 g/min–8 g/min <2nd to 6th Times>
spray nozzle type: side spray, spray nozzle position: lower, air supply temperature: 70° C.–80° C., air exhaust temperature: 32° C.–42° C., air flow: 30–55 m$^3$/h, rotation rate of rotor plate: 200 rpm–350 rpm, spray air pressure: 2.2 kgf/cm$^2$–3.0 kgf/cm$^2$, spray air flow: 40 L/min–70 L/min, side air flow: 40 L/min–50 L/min, spray rate (flow rate): 3 g/min–8 g/min

Example 10

Figure 18:
FIG. 18 is a photograph showing a single crystal of sodium chloride used as a drug nucleus in Example 10.
Figure 19:
FIG. 19 is a photograph showing the drug granules obtained in Example 10.

Using a rotary fluidized bed granulate coating apparatus (Multiplex MP-01, POWREX CORPORATION), an aqueous sodium chloride solution (26%, w/w, dissolved at 25° C.) was gradually sprayed on the single crystals of sodium chloride (FIG. 18) charged in the apparatus in advance. The granules were classified to give 524 g of drug granules (FIG. 19) only of sodium chloride (500–1000 μm) on the way to spheres.

The production conditions were as follows.
spray nozzle type: top spray, spray nozzle position: lower, air supply temperature: 73° C.–78° C., air exhaust temperature: 36° C.–40° C., air flow: 50 m$^3$/h, rotation rate of rotor plate: 150 rpm–250 rpm, spray air pressure: 1.2 kgf/cm$^2$–1.6 kgf/cm$^2$, spray air flow: 25 L/min, spray rate (flow rate): 8 g/min–14 g/min In Table 7, the charge amounts of single crystals of each drug, formulation conditions of the spray solution (aqueous solution of each drug) and the obtained amount are shown.

TABLE 7

| Drug | ethydronate disodium | cimetidine | sodium chloride |
|---|---|---|---|
| charge amount | 400 | 500 | 400 |
| spray solution | | | |
| drug | 400 | 250 | 400 |
| purified water | 1333 | 500 | 1133 |
| pH adjusting agent | — | 80 | — |
| Obtained amount | 615 | 438 | 524 |

Unit: g

Evaluation Test 3

The granular strength was measured using a table-top material tester (EZ Test-20N, Shimadzu Corporation).

From the drug granules obtained in Example 1 (granulation 9 times), Example 7 and Example 9 (granulation 4 times), those having a particle size of 500 μm±50 μm were selected and one drug granule each was placed on a sample table of the table-top material tester. Using an upper compression jig having a diameter of 5 mm, the granules were compressed in a compression mode at 0.5 mm/min and the maximum peak was taken as the strength. The measurement was repeated 10 times and the measures were averaged. The strength was divided by the sectional area of the drug granule for each drug.

The granular strength was 907 gf/mm$^2$ for granules of Example 1, 799 gf/mm$^2$ for granules of Example 7 and 1233 gf/mm$^2$ for granules of Example 9.

The "long/short diameter ratio" of the drug granules of Example 1 (granulation 7 times) and Example 9 (granulation 4 times) was measured. The drug granules were placed at random on a slide glass for microscopes, photographed and the length of the longest axis (long diameter) and the length of short axis (short diameter), perpendicularly drawn from the middle point of the length of the long axis, of each of the ten drug granules was measured. The ratio of the long diameter to the short diameter was determined for each of the 10 granules and the measures were averaged.

The "specific volume" of the drug granules of Example 1 (granulation 7 times) and Example 9 (granulation 4 times) was measured. The specific volume is determined by dropping drug granules having a weight "W" (ca. 30 g) gradually at a constant rate from right above of a 100 ml measuring cylinder and, after dropping, reading the volume of standing granules. That is, the volume "V" (ml) was divided by weight "W" (g) of the dropped granules and 5 measures were averaged.

The "angle of repose" of the drug granules of Example 1 (granulation 7 times) and Example 9 (granulation 4 times) was measured. A cylindrical disc having a diameter of 5 cm was kept horizontally and drug granules were gradually dropped from about 1 cm above the center of the cylindrical disc at a constant rate. Since the granules formed a bank, the point from which the granules were dropped was raised to keep about 1 cm from the top of the bank. When the cylindrical disc was entirely covered with the granules and a cone was formed with the granules, an angle formed by the upper part of the inclination formed by the granules with the horizontal plane (upper surface of the cylindrical disc) was read with a protractor on the periphery of the cylindrical disc. The measurement value was an average of two measures.

Drug Granules of Example 1 (Granulation 7 Times)
long/short diameter ratio 1.1, specific volume 1.45 g/ml, angle of repose 32 degrees Drug Granules of Example 9 (Granulation 4 Times)
long/short diameter ratio 1.1, specific volume 1.09 g/ml, angle of repose 32.5 degrees As is evident from the foregoing explanation, the present invention affords a pharmaceutical preparation containing a water soluble drug as an active ingredient at a high density, which is superior in uniform content and stability.

In addition, the present invention affords drug granules capable of affording a pharmaceutical preparation superior in drug release control and having a reduced size as compared to conventional ones, and a production method thereof.

The present invention further provides coated granules using drug granules containing a water soluble drug as an active ingredient at a high density, which is superior in uniform content and stability, and a production method thereof.

The present invention also provides a pharmaceutical preparation containing a water soluble drug as an active ingredient at a high density and substantially free of a binder, which is superior in uniform content and stability.

The present invention further provides granules of an water soluble drug substantially free of a binder, and a production method thereof.

The present invention moreover affords coated granules using drug granules containing a water soluble drug as an active ingredient at a high density and substantially free of a binder, which is superior in uniform content and stability, and a production method thereof.

This application is based on patent application No. 64056/2001 filed in Japan, the contents of which are hereby incorporated by reference.

The invention claimed is:

1. A method of manufacturing a drug granule, comprising a granulation step of spraying only a solution of a water soluble drug on a crystal of said water soluble drug substantially without using a binder or in the absence of binder in a rotary fluidized bed granulate coating apparatus, wherein the drug granule has a granular strength of 650–2500 gf/mm$^2$, and wherein the drug is selected from the group consisting of metformin hydrochloride, ethydronic acid di-sodium, cimetidine, carbocistein, gabapentin, ciprofloxacin hydrochloride, mexiletine hydrochloride and vancomycin hydrochloride.

2. A method of manufacturing a coated granule, which comprises:
(a) spraying a solution of a water soluble drug on a crystal of said water soluble drug obtained by a method comprising a granulation step of spraying only a solution of a water soluble drug on a crystal of said water soluble drug substantially without using a binder or in the absence of binder in a rotary fluidized bed granulate coating apparatus to form a drug granule,
wherein the drug granule has a granular strength of 650–2500 gf/mm$^2$ and the drug is selected from the group consisting of metformin hydrochloride, ethydronic acid di-sodium, cimetidine, carbocistein, gabapentin, ciprofloxacin hydrochloride, mexiletine hydrochloride and vancomycin hydrochloride; and
(b) coating said drug granule with a release control film coating agent.

* * * * *

UNITED STATES PATENT AND TRADEMARK OFFICE
CERTIFICATE OF CORRECTION

PATENT NO. : 7,192,608 B2  
APPLICATION NO. : 10/091559  
DATED : March 20, 2007  
INVENTOR(S) : Yasushi Ochiai et al.

Page 1 of 1

It is certified that error appears in the above-identified patent and that said Letters Patent is hereby corrected as shown below:

On the Title Page (73):

The Assignee name reads "Sumitomo Pharmaceuticals Company Limited" should read --Dainippon Sumitomo Pharma Co., Ltd--.

Signed and Sealed this

Sixteenth Day of October, 2007

JON W. DUDAS  
*Director of the United States Patent and Trademark Office*